US006833542B2

(12) United States Patent
Wang et al.

(10) Patent No.: US 6,833,542 B2
(45) Date of Patent: Dec. 21, 2004

(54) METHOD FOR SORTING PARTICLES

(75) Inventors: Mark M. Wang, San Diego, CA (US); Eugene Tu, San Diego, CA (US); James P. O'Connell, Del Mar, CA (US); Kristie L. Lykstad, San Diego, CA (US); William F. Butler, La Jolla, CA (US)

(73) Assignee: Genoptix, Inc., San Diego, CA (US)

( * ) Notice: Subject to any disclaimer, the term of this patent is extended or adjusted under 35 U.S.C. 154(b) by 341 days.

(21) Appl. No.: 09/993,376

(22) Filed: Nov. 14, 2001

(65) Prior Publication Data

US 2002/0132316 A1 Sep. 19, 2002

Related U.S. Application Data

(63) Continuation-in-part of application No. 09/845,245, filed on Apr. 27, 2001.
(60) Provisional application No. 60/248,451, filed on Nov. 13, 2000.

(51) Int. Cl.[7] ............................. H01S 3/00; C12N 13/00
(52) U.S. Cl. ..................................... 250/251; 435/173.1
(58) Field of Search ......................... 250/251; 435/173.1

(56) References Cited

U.S. PATENT DOCUMENTS

| 3,558,877 A | 1/1971 | Pressman |
| 3,628,182 A | 12/1971 | Ashkin et al. |
| 3,638,139 A | 1/1972 | Ashkin et al. |
| 3,662,183 A | 5/1972 | Ashkin et al. |
| 3,710,279 A | 1/1973 | Askin |
| 3,725,810 A | 4/1973 | Ashkin et al. |
| 3,761,721 A | 9/1973 | Altshuler et al. |
| 3,778,612 A | 12/1973 | Ashkin |
| 3,793,541 A | 2/1974 | Ashkin et al. |
| 3,808,432 A | 4/1974 | Ashkin |
| 3,808,550 A | 4/1974 | Ashkin |
| 4,063,106 A | 12/1977 | Ashkin et al. |
| 4,092,535 A | 5/1978 | Ashkin et al. |
| 4,127,329 A | 11/1978 | Chang et al. |
| 4,247,815 A | 1/1981 | Larson et al. |

(List continued on next page.)

FOREIGN PATENT DOCUMENTS

| DE | 4326181 A1 | 2/1995 |
| EP | 0635994 B1 | 9/1998 |
| EP | 0556748 B1 | 10/1998 |

(List continued on next page.)

OTHER PUBLICATIONS

Ackerson et al, Radiation Pressure As A Technique For Manipulating The Particle Order In Colloidal Suspensions, Faraday, Discuss.Chem.Soc., 83, 1987, pp 309–316.

(List continued on next page.)

*Primary Examiner*—Jon P. Weber
(74) *Attorney, Agent, or Firm*—O'Melveny & Myers LLP

(57) ABSTRACT

A method for sorting a particle of interest from a plurality of particles includes the steps of determining an absorption maxima of the particle of interest, providing a light source for generating a beam of coherent light at a wavelength correlating to the absorption maxima, providing a plurality of particles on a support surface, and imparting relative motion between the beam of coherent light and the plurality of particles so as to cause differential movement between the particle of interest and the plurality of particles. The particle of interest is then collected.

6 Claims, 19 Drawing Sheets

U.S. PATENT DOCUMENTS

| | | |
|---|---|---|
| 4,253,846 A | 3/1981 | Smythe et al. |
| 4,327,288 A | 4/1982 | Ashkin et al. |
| 4,386,274 A | 5/1983 | Altshuler |
| 4,390,403 A | 6/1983 | Batchelder |
| 4,440,638 A | 4/1984 | Judy et al. |
| 4,451,412 A | 5/1984 | Loiseaux et al. |
| 4,453,805 A | 6/1984 | Ashkin et al. |
| 4,520,484 A | 5/1985 | Huignard et al. |
| 4,536,657 A | 8/1985 | Bruel |
| 4,627,689 A | 12/1986 | Asher |
| 4,632,517 A | 12/1986 | Asher |
| 4,756,427 A | 7/1988 | Gühde |
| 4,827,125 A | 5/1989 | Goldstein |
| 4,886,360 A | 12/1989 | Finlan |
| 4,887,721 A | 12/1989 | Martin et al. |
| 4,893,886 A | 1/1990 | Ashkin |
| 4,908,112 A | 3/1990 | Pace |
| 5,029,791 A | 7/1991 | Ceccon et al. |
| 5,079,169 A | 1/1992 | Chu et al. |
| 5,100,627 A | 3/1992 | Buican et al. |
| 5,113,286 A | 5/1992 | Morrison |
| 5,121,400 A | 6/1992 | Verdiell et al. |
| 5,170,890 A | 12/1992 | Wilson et al. |
| 5,189,294 A | 2/1993 | Jackson et al. |
| 5,198,369 A | 3/1993 | Itoh et al. |
| 5,206,504 A | 4/1993 | Sridharan |
| 5,212,382 A | 5/1993 | Sasaki et al. |
| 5,245,466 A | 9/1993 | Burns et al. |
| 5,274,231 A | 12/1993 | Chu et al. |
| 5,283,417 A | 2/1994 | Misawa et al. |
| 5,308,976 A | 5/1994 | Misawa et al. |
| 5,327,515 A | 7/1994 | Anderson et al. |
| 5,337,324 A | 8/1994 | Ohtsu et al. |
| 5,338,930 A | 8/1994 | Chu et al. |
| 5,343,038 A | 8/1994 | Nishiwaki et al. |
| 5,355,252 A | 10/1994 | Haraguchi |
| 5,360,764 A | 11/1994 | Celotta et al. |
| 5,363,190 A | 11/1994 | Inaba et al. |
| 5,364,744 A | 11/1994 | Buican et al. |
| 5,374,566 A | 12/1994 | Iranmanesh |
| 5,445,011 A | 8/1995 | Ghislain et al. |
| 5,452,123 A | 9/1995 | Asher et al. |
| 5,473,471 A | 12/1995 | Yamagata et al. |
| 5,495,105 A | 2/1996 | Nishimura et al. |
| 5,512,745 A | 4/1996 | Finer et al. |
| 5,608,519 A | 3/1997 | Gourley et al. |
| 5,620,857 A | 4/1997 | Weetall et al. |
| 5,625,484 A | 4/1997 | Coutsomitras |
| 5,629,802 A | 5/1997 | Clark |
| 5,631,141 A | 5/1997 | Sonek et al. |
| 5,637,458 A | 6/1997 | Frankel et al. |
| 5,644,588 A | 7/1997 | Misawa |
| 5,653,859 A | 8/1997 | Parton et al. |
| 5,659,561 A | 8/1997 | Torruellas et al. |
| 5,689,109 A | 11/1997 | Schutze |
| 5,694,216 A | 12/1997 | Riza |
| 5,760,395 A | 6/1998 | Johnstone |
| 5,770,856 A | 6/1998 | Fillardes et al. |
| 5,773,298 A | 6/1998 | Lynggaard et al. |
| 5,776,674 A | 7/1998 | Ulmer |
| 5,793,485 A | 8/1998 | Gourley |
| 5,795,457 A | 8/1998 | Pethig et al. |
| 5,804,436 A | 9/1998 | Okun et al. |
| 5,814,200 A | 9/1998 | Pethig et al. |
| 5,858,192 A | 1/1999 | Becker et al. |
| 5,888,370 A | 3/1999 | Becker et al. |
| 5,900,160 A | 5/1999 | Whitesides et al. |
| 5,919,646 A | 7/1999 | Okun et al. |
| 5,935,507 A | 8/1999 | Morito et al. |
| 5,939,716 A | 8/1999 | Neal |
| 5,942,443 A | 8/1999 | Parce et al. |
| 5,950,071 A | 9/1999 | Hammond et al. ......... 438/115 |
| 5,952,651 A | 9/1999 | Morito et al. |
| 5,953,166 A | 9/1999 | Shikano et al. |
| 5,956,106 A | 9/1999 | Petersen et al. |
| 5,993,630 A | 11/1999 | Becker et al. |
| 5,993,631 A | 11/1999 | Parton et al. |
| 5,993,632 A | 11/1999 | Becker et al. |
| 6,015,714 A | 1/2000 | Baldarelli et al. |
| 6,033,546 A | 3/2000 | Ramsey |
| 6,055,106 A | 4/2000 | Grier et al. |
| 6,067,859 A | 5/2000 | Kas et al. |
| 6,071,394 A | 6/2000 | Cheng et al. |
| 6,078,681 A | 6/2000 | Silver |
| 6,082,205 A | 7/2000 | Zborowski et al. |
| 6,088,097 A | 7/2000 | Uhl |
| 6,088,376 A | 7/2000 | O'Brien et al. |
| 6,096,509 A | 8/2000 | Okun et al. |
| 6,111,398 A | 8/2000 | Graham |
| 6,121,603 A | 9/2000 | Hang et al. |
| 6,139,831 A | 10/2000 | Shivashankar et al. |
| 6,142,025 A | 11/2000 | Zborowski et al. |
| 6,143,558 A | 11/2000 | Kopelman et al. |
| 6,149,789 A | 11/2000 | Benecke et al. |
| 6,197,176 B1 | 3/2001 | Pethig et al. |
| 6,208,815 B1 | 3/2001 | Seidel et al. |
| 6,215,134 B1 | 4/2001 | O'Brien et al. |
| 6,221,654 B1 | 4/2001 | Quake et al. |
| 6,224,732 B1 | 5/2001 | Imasaka et al. |
| 6,242,209 B1 | 6/2001 | Ransom et al. |
| 6,280,960 B1 | 8/2001 | Carr ......................... 435/7.2 |
| 6,280,967 B1 | 8/2001 | Ransom et al. |
| 6,287,758 B1 | 9/2001 | Okun et al. |
| 6,287,776 B1 | 9/2001 | Hefti |
| 6,287,832 B1 | 9/2001 | Becker et al. |
| 6,287,874 B1 | 9/2001 | Hefti |
| 6,294,063 B1 | 9/2001 | Becker et al. |
| 6,344,325 B1 | 2/2002 | Quake et al. |
| 6,399,397 B1 | 6/2002 | Zarling et al. |
| 6,514,722 B2 | 2/2003 | Palsson et al. |
| 2002/0058332 A1 | 5/2002 | Quake et al. |
| 2003/0032204 A1 | 2/2003 | Walt et al. |
| 2003/0047676 A1 | 3/2003 | Grier et al. |

FOREIGN PATENT DOCUMENTS

| | | |
|---|---|---|
| EP | 0898493 | 1/2000 |
| JP | 3-101419 | 4/1991 |
| JP | 5-88107 | 4/1993 |
| JP | 5-232398 | 9/1993 |
| JP | 6-123886 | 5/1994 |
| JP | 6-132000 | 5/1994 |
| JP | 8-234110 | 9/1996 |
| JP | 4-43434 A | 2/1997 |
| JP | 10-48102 | 2/1998 |
| JP | 10-62332 | 3/1998 |
| JP | 11-218691 | 8/1999 |
| WO | WO 94/08221 | 4/1994 |
| WO | WO 97/21832 | 6/1997 |
| WO | WO 99/39190 | 8/1999 |
| WO | WO 99/61888 | 12/1999 |
| WO | WO 00/23825 | 4/2000 |
| WO | WO 00/45160 | 8/2000 |
| WO | WO 00/45170 | 8/2000 |
| WO | WO 00/45179 | 8/2000 |
| WO | WO 00/54882 | 9/2000 |
| WO | WO 01/05514 | 1/2001 |
| WO | WO 01/09606 | 2/2001 |
| WO | WO 01/11333 A3 | 2/2001 |
| WO | WO 01/14870 | 3/2001 |
| WO | WO 01/20329 | 3/2001 |
| WO | WO 01/32930 | 5/2001 |

| | | |
|---|---|---|
| WO | WO 01/40454 A1 | 6/2001 |
| WO | WO 01/40769 | 6/2001 |
| WO | WO 01/44852 | 6/2001 |
| WO | WO 01/11333 B1 | 9/2001 |
| WO | WO 01/68110 A1 | 9/2001 |
| WO | WO 02/22774 A1 | 3/2002 |

OTHER PUBLICATIONS

Afzal t al, Optical Tweezers Using A Diode Laser, Rev.Sci. Instrum., 63,4, 04/1992, pp 2157–2163.

Amato, Optical Matter Emerges Under Laser, Science News, 136, 1989, pp 212.

Asher et al, Crystalline Colloidal Bragg Diffraction Devices: The Basis For A New Generation Of Raman Instrumentation, Spectroscopy, 1,12, 1986, pp. 26–31.

Ashkin, Acceleration & Trapping Of Particles By Radiation Pressure, Physical Review Letters, 24,4 Jan. 26, 1970, pp 156–159.

Ashkin, Trapping Of Atoms By Resonance Radiation Pressure, Physical Review Letters, 40, 12, Mar. 20, 1978, pp 729–732.

Ashkin, Applications Of Laser Radiation Pressure, Science, 210, 4474, Dec. 5, 1980, pp 1081–1088.

Ashkin, Forces Of A Single Beam Gradient Laser Trap On A Dielectric Sphere In The Ray Optics Regime, Biophys. J., 61, 02/1992, pp 569–582.

Ashkin et al, Optical Levitation Of Liquid Drops By Radiation Pressure, Science, 187, 4181, Mar. 21, 1975, pp 1073–1075.

Ashkin et al, Observation Of A Single Beam Gradient Force Optical Trap For Dielectric Particles, Optics Letters, 11,5, 05/1986, pp 288–290.

Ashkin et al, Optical Trapping & Manipulation Of Viruses & Bacteria, Science, 235, 4795, Mar. 20, 1987, pp 1517–1520.

Ashkin et al, Optical Trapping & Manipulation Of Single Cells Using Infrared Laser Beams, Nature, 330, 6150, 12/24–31/1987, pp 769–771.

Ashkin, Internal Cell Manipulation Using Laser Traps, PNAs USA, 86, 20, 10/1989, pp 7914–7918.

Ashkin, Optical Levitation By Radiation Pressure, Appl. Phys.Lett., 19,8, Oct. 15, 1971, pp 283–285.

Ashkin, Optical Trapping & Manipulation Of Neutral Particles Using Lasers, PNAs USA, 94,10, May 13, 1997, pp 4853–4860.

Aviva, Avia website printout, www.avivabio.com.

Bagnato et al, Continuous Stopping & Trapping Of Neutral Atoms, Physical Review Letters, 58,21, May 25, 1987, pp 2194–2197.

Becker et al, Separation Of Human Breast Cancer Cells From Blood By Differential Dielectric Affinity, PNAs USA, 92, 01/1995, pp 860–864.

Berns et al, Use Of a Laser Induced Optical Force Trap To Study Chromosome Movement On The Mitotic Spindle, Proc.Natl.Acad.Sci.USA, 86,12, 06/1989, pp 4539–4543.

Berns et al, Laser Microbeam As A Tool In Cell Biology, Intl Review of Cytology, 129, 1991, pp 1–44.

Bigelow et al, Observation Of Channeling Of Atoms In The Three Dimensional Interference Pattern Of Optical Standing Waves, Physical Review Letters, 65,1, Jul. 2, 1990, pp 29–32.

Block et al, Compliance Of Bacterial Flagella Measuremtn Without Temperatures, Nature, 338, Apr. 6, 1989, pp 514–518.

Block, Optical Tweezers: A New Tool For Biophysics, Noninvasiv Techniques In Cell Biology, chap 15, 1990, pp 375–402.

Bronkhorst et al, A New Method To Study Shape Recovery Of Red Blood Cells Using Multiple Optical Trapping, Biophys. J., 69,5, 11/1995, pp 1666–1673.

Buican et al, Automated Single Cell Manipulation & Sorting By Light Trapping, Applied Optics, 26, 24, Dec. 15, 1987, pp 5311–5316.

Burns et al, Optical Binding, Physical Review Letters, 63,12, Sep. 18, 1989, pp 1233–1236.

Burns et al, Optical Matter: Crystallization & Binding In Intense Optical Fields, Science, 249, 4970, Aug. 17, 1990, pp 749–754.

Business Week, Is There Anything A Laser Can't Do?, Business Week, Oct. 30, 1989, pp 157.

Bustamante, Direct Observation & Manipulation Of Single DNA Molecules Using Fluorescence Microscopy, Annu.Rev.Biophys.Biophys.Chem., 20, 1991, pp 415–446.

Bustamante et al, Towards A Molecular Description Of Pulsed Field Gel Electrophoresis, TibTech, 11, 1993, pp 23–30.

Bustamante et al, Manipulation Of Single DNA Molecules & Measurement Of Their Persistence, Length & charge Density Under A Fluorescence Microscope, Abst of the 19th Ann Mfg Of Amer. Soc. For Photobiology, Photochem Photobiol, 53, Jun. 22, 1991, pp 46S.

Chiou et al, Interferometric Optical Tweezers, Optics Communications, 133, Jan. 1, 1997, pp 7–10.

Chou et al, A Microfabricated Device For Sizing & Sorting DNA Molecules, PNAs USA, 96, 01/1999, pp 11–13.

Chowdhury et al, Laser Induced Freezing, Physical Review Letters, 55,8, Aug. 19, 1985, pp 833–836.

Chowdhury et al, All Optical Logic Gates Using Colloids, Microwave & Optical Technology Letters, 1,5, 07/1988, pp 175–178.

Chowdhury et al, Exchange of Letters, Science, 252, May 25, 1991.

Chu et al, Experimental Observation Of Optically Trapped Atoms, Physical Review Letters, 57,3, Jul. 21, 1986, pp 314–317.

Clark et al, Single Colloidal Crystals, Nature, 281, 5726, Sep. 6, 1979, pp 57–60.

Crocker et al, Microscopic Measurement Of The Pair Interaction Potential Of Charge Stabilized Colloid, Physical Review Letters, 73,2, Jul. 11, 1994, pp 352–355.

Cromie, Scientists Bind Matter With Light, Harvard University Gazette, Oct. 13, 1989, 1, pp 4–5.

Dufresne et al, Optical Tweezer Arrays & Optical Substrates Created With Diffractive Optics, Review of Scientific Instruments, 69, 5, 05/1998, pp 1974–1977.

Fallman et al, Design For Fully Steerable Dual Trap Optical Tweezers, Applied Optics, 36,10, Apr. 1, 1997, pp 2107–2113.

Fisher, The Light That Binds, Popular Science, Jan. 24, 1990, pp 24–25.

Fournier et al, Writting Diffractive Structures By Optical Trapping, SPIE, 2406, 02/06–08/1995, pp 101–112.

Fu et al, A Microfabricated Fluorescence Activated Cell Sorter, Nature Biotechnology, 17, 11/1999, pp 1109–1111.

Gascoyne, Gascoyne website printout, Dec. 1, 2000.

Gorre–Talini et al, Sorting Of Brownian Particles By The Pulsed Application Of A Asymmetric Potential, Physical Review E, 56, 2, Aug. 1997, pp 2025–2034.

Grier, New Age Crystals, Nature, 389, 6653, Oct. 23, 1997, pp 784–785.

Greulich et al, The Light Microscope On Its Way From An Analytical T A Preparative Tool, Jnl Of Microscopy, 167, Pt 2, Aug. 1, 1992, pp 127–151.

Gurrieri et al, Imaging Of Kinked Configurations Of DNA Molecules Undergoing Orthogonal Field Alternating Gel Electrophoresis By Fluorescence Microscopy, Biochemistry, 29, 13, Apr. 3, 1990, pp 3396–3401.

Gurrieri et al, Trapping Of Megabase Sized DNA Molecules During Agarose Gel Electrophoresis, PNAs USA, 96, 01/1999, pp 453–458.

Holtz et al, Polymerized Colloidal Crystal Hydrogel Films As Intelligent Chemical Sensing Materials, Nature, 389, Oct. 23, 1997, pp 829–832.

Houseal et al, Imaging Of The Motions & Conformational Transitions Of Single DNA Molecules Using Fluorescence Microscopy, Biophys. J., 55, 324, Feb. 12, 1989, pp 373a.

Houseal et al, Real Time Imaging Of Single DNA Molecules With Fluorescence Microscopy, Biophys. J., 56, 09/1989, pp 507–516.

Huber et al, Isolation Of A Hyperthermophillic Archaeum Predicted By in situ RNA Analysis, Nature, 376, 6535, Jul. 6, 1995, pp 57–58.

Inside R&D, Matter Bound By Light, Inside R&D, 18, 43, Oct. 25, 1989, pp 2.

Kuo et al, Optical Tweezers In Cell Biology, Trends In Cell Biology, 2, 04/1992, pp 116–118.

Lai, Determination Of Spring Constant Of Laser Trapped Particle By Self–Mining Interfermetry, Proc.of SPIE, 3921, 2000, pp 197–204.

Law, Matter Rides On Ripples of Lights, New Scientist, 1691, Nov. 18, 1989, pp 1691.

Leger et al, Coherent Laser Addition Using Binary Phase Gratings, Applied Optics, 26,20, Oct. 15, 1987, pp 4391–4399.

Mammen et al, Optically Controlled Collisions Of Biological Objects To Evaluate Potent Polyvalent Inhibitors Of Virus–Cell Adhesion, Chemistry & Biology, 3, 9, 09/1996, pp 757–763.

Mason et al, Optical Measurements Of Frequency Dependent Linear Viscoelastic Modull Of Complex Fluids, Physical Review Letters, 74,7, Feb. 13, 1995, pp 1250–1253.

McClelland et al, Low Frequency Peculiarities Of The Photorefractive Response In Sillenites, Optics Communications, 113, Jan. 1, 1995, pp 371–377.

Misawa et al, Spatial Pattern Formation, Size Selection & Directional Flow Of Polymer Latex Particles By Laser Trapping Technique, Chemistry Letters, 3, 03/1991, pp 469–472.

Misawa et al, Multibeam Laser Manipulation & Fixation Of Microparticles, Appl.Phys.Lett., 60,3, Jan. 20, 1992, pp 310–312.

Mitchell et al, A Practical Optical Trap For Manipulation & Isolating Bacteria From Complex Microbial Communities, Microb Ecol, 25, 2, 1993, pp 113–119.

Murray et al, Experimental Observation Of Two Stage Melting In A Classical Two Dimensional Screened Coulomb System, Physical Review Letters, 58,12, Mar. 23, 1987, pp 1200–1203.

Murray et al, Colloidal Crystals, American Scientist, 83,3, 05–06/1995, pp 238–245.

Mycometrix, Mycometrix Website printout, http:www/mycometrix.com, Dec. 1, 2000.

New York Times, Atoms Bound Together By Light, New York Times, Oct. 31, 1989, pp C17.

Paterson et al, Controlled Rotation Of Optically Trapped Microscopic Particles, Science, 292, May 4, 2001, pp 912–914.

Pritchard et al, Light Traps Using Spontaneous Forces, Physical Review Letters, 57,3, Jul. 21, 1986, pp 310–313.

Quake et al, From Micro– To Nanofabrication With Soft Materials, Science, 290, Nov. 24, 2000, pp 1536–1540.

Raab t al, Trapping Of Neutral Sodium Atoms With Radiation Pressure, Physical Review Letters, 59,23, Dec. 7, 1987, pp 2631–2634.

Rogovin et al, Bifurcation In Degenerate Four–Wave Mixing In Liquid Suspensions Of Microspheres, Physical Review Letters, 54,20, May 20, 1985, pp 2222–2225.

Roosen, A Theoretical & Experimental Study Of The Stable Equillibrium Positions Of Spheres Levitated By Two Horizontal Laser Beams, Optics Communications, 21, 1, 04/1977, pp 189–194.

Sasaki et al, Laser Scanning Micromanipulation & Spatial Patterning Of Fine Particles, Japn Jnl Of Applied Physics, 31,5B, 05/1991, pp L907–L909.

Sasaki et al, Pattern Formation & Flow Control Of Fine Particles By Laser Scanning Micromanipulation, Optics Letters, 16,19, Oct. 1, 1991, pp 1463–1465.

Sasaki et al, Optical Micromanipulation Of A Lasing Polymer Particle In Water, Jpn.J.Appl.Phys., Pt2, 32, 8B, Aug. 15, 1993, pp L1144–1147.

Smith et al, Four–wave Mixing In An Artificial Kerr Medium, Optics Letters, 6, 6, 06/1981, pp 284–286.

Smith et al, Direct Mechanical Measurements Of The Eleasticity Of Single DNA Molecules By Using Magnetic Beads, Science, 258, 5085, Nov. 13, 1992, pp 1122–1126.

Smith et al, Model & Computer Simulations Of the Motion Of DNA Molecules During Pulse Field Gel Electrophoresis, Biochemistry, 30, 21, May 28, 1991, pp 5264–5274.

Suzuki et al, Hysteretic Behavior & Irreversibility Of Polymer Gels By pH Change, J.Chem.Phys., 103, 11, Sep. 15, 1995, pp 4706–4710.

Suzuki et al, Optical Switching In Polymer Gels, J.Appl. Phys., 80,1, Jul. 1, 1996, pp 131–136.

Svoboda et al, Biological Applications Of Optical Forces, Annu.Rev.Biophys.Biomol.Struct., 23, 1994, pp 247–285.

Svoboda et al, Conformation & Elasticity Of The Isolated Red Blood Cell Membrane Skeleton, Biophys.J., 63, 3, Sep. 1, 1992, pp 784–793.

Swanson et al, Diffractive Optical Elements For use In Infrared Systems, Optical Engineering, 28,6, 06/1989, pp 605–608.

Takashima et al, Dielectric Dispersion Of DNA, J.Mol.Biol., 7, 5, 11/1963, pp 455–467.

Thirunamachandran, Intramolecular Interactions In The Presence Of An Intense Radiation Field, Molecular Physics, 40,2, 1980, pp 393–399.

Unger et al, Monolithic Microfabricated Valves & Pumps By Multilayer Soft Lithography, Science, 288, Apr. 7, 2000, pp 113–116.

Van Blaaderen et al, Template Directed Colloidal Crystallization, Nature, 385, 6614, Jan. 23, 1997, pp 321–324.

Visscher et al, Construction Of Multiple Beam Optical Traps With Nanometer Resolution Position Screening, IEEE Jnl Of Selected Topics In Quantum Electronics, 2,4, 12/1996, pp 1066–1075.

Weber et al, Manipulation Of Cells, Organelles & Genomes By Laser Microbeam & Optical Trap, Intl Rev Of Cytology, 133, 1992, pp 1–41.

Westbrook et al, Localization Of Atoms In A Three Dimensional Standing Wave, Physical Review Letters, 65,1, Jul. 2, 1990, pp 33–36.

Wheeler, Force Fields Of Laser Light Bind Molecules In A Remarkable Discovery At Harvard, The Chronicle Of Higher Education, Oct. 25, 1989, pp A4.

Wright t al, Radiation Trapping Forces On Microspheres With Optical Tweezers, Appl.Phys.L tt, 63, 6, Aug. 9, 1993, pp 715–717.

Wuite et al, An Integrated Laser Trap/Flow Control Video Microscope For The Study Of Single Biomolecules, Biphysical Jnl, 79,2, 08/2000, pp 1155–1167.

Xiang et al, A Combinatorial Approach To Materials Discovery, Science, 268, 5218, Jun. 23, 1995, pp 1738–1740.

Yablonovitch et al, Inhibited Spontaneous Emission In Solid State Physics & Electronics, Physical Review Letters, 58,20, May 18, 1987, pp 2059–2062.

Yablonovitch et al, Photonic Band Structure: The Face Centered Cubic Face, Physical Review Letters, 63,18, Oct. 30, 1989, pp 1950–1953.

Yuqiu, Mechanical, Electrical, & Chemical Manipulation Of Single DNA Molecules, Nanotechnology, 3, 1992, pp 16–20.

Ashkin et al, "Force Generation Of Organelle Transport Measured In Vivo By An Infrared Laser Trap", Nature, 348, Nov. 22, 1990, 346–348.

Caldwell, "Field–Flow Fractionation", Analytical Chemistry, 60, 17, Sep. 1, 1988, 959–971.

Davies et al, "Optically Controlled Collisions Of Biological Objects", SPIE, 3260, 1/25–28/98, 15–22.

Esener, Center For Chips With Heterogeneously Integrated Photonics (CHIPS), DARPA Opto Centers Kickoff, Nov. 8, 2000, Dana Point, CA.

Flynn et al, "Parallel Transport Of Biological Cells Using Individually Addressable VCSEL Arrays As Optical Tweezers", Sensors & Actuators B, 87, 2002, 239–243.

Sasaki et al, "Optical Trapping Of A Metal Particle & A Water Droplet By A Scanning Laser Beam", Appl. Phys. Lett., 60, 7, Feb. 17, 1992, 807–809.

Shikano et al, "Separation Of A Single Cell By Red–Laser Manipulation", Applied Physics Letters, 75, 17, Oct. 25, 1999, 2671–2673.

Sonek et al, "Micromanipulation & Physical Monitoring Of Cells Using Two–Photon Excited Fluorescence In CW Laser Tweezers", SPIE, 2678, 01/28–Feb. 1, 1996, 62–68.

Wang et al, "All Optical Switching Of Biological Samples In A Microfluidic Device", International Phonics Conference 2000, 12/12–15/00, Hsinchu, Taiwan.

Wang et al, "Integration Of Optoelectronic Array Devices For Cell Transport & Sorting", Photonics West 2001, 01/20–26/01, San Jose, CA.

Wei et al, Laser Trapping Microscopy As A Diagnostic Technique For The Study Of Cellular Response & Laser–Cell Interactions, SPIE, 2983, 02/10–11/97, 22–28.

Zahn et al, "Fluorimetric Multiparameter Cell Assay At The Single Cell Level Fabricated By Optical Tweezers", FEBS Letters, 443, 1999, 337–340.

Imasaka et al, "Optical Chromatography", Analytical Chemistry, 67, 11, Jun. 1, 1995, 1763–1765.

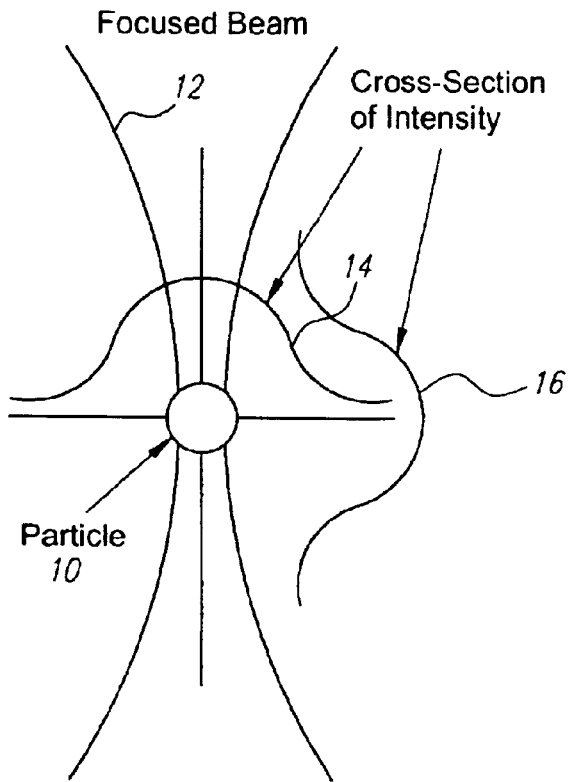

$$F_\nabla = 2\pi \cdot r^3 \frac{\sqrt{\varepsilon_B}}{c} \left(\frac{\varepsilon - \varepsilon_B}{\varepsilon + 2\varepsilon_B}\right)(\nabla \cdot I)$$

$F_\nabla$ = Optical force on particle towards higher intensity r = Radius of particle $\varepsilon_B$ = Dielectric constant of backround medium $\varepsilon$ = Dielectric constant of particle I = Light intensity (W/cm$^2$)

$\nabla$ = Spatial derivative

*FIG. 1*

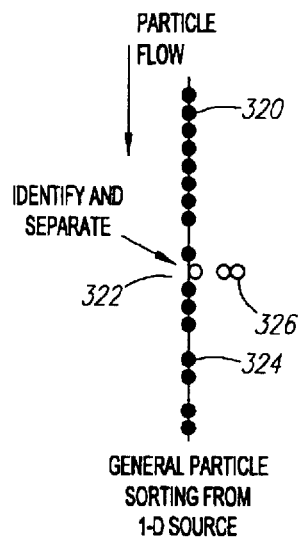
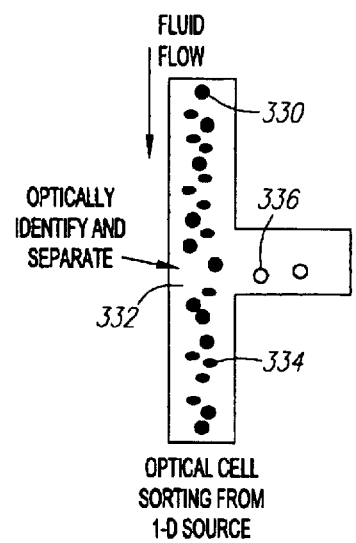
FIG. 14A
FIG. 14B
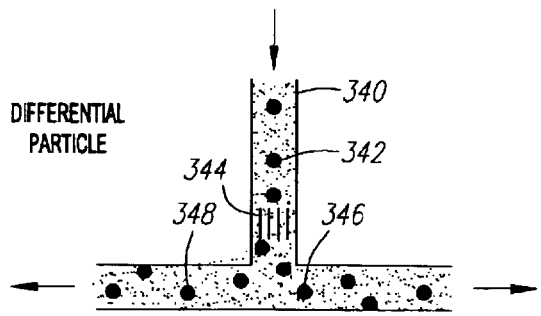
FIG. 15
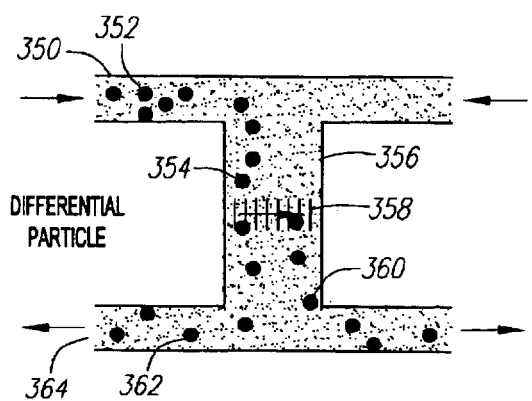
FIG. 16
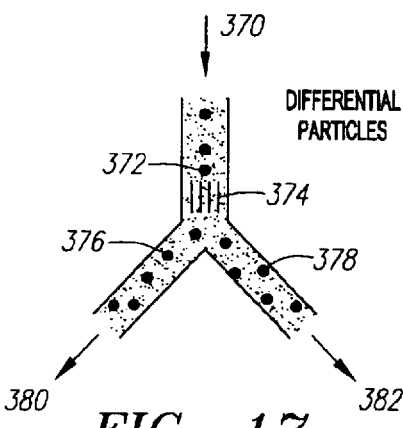
FIG. 17
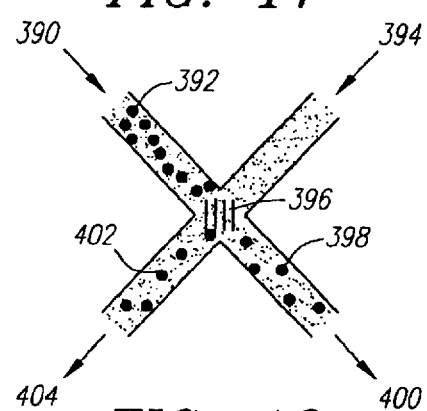
FIG. 18

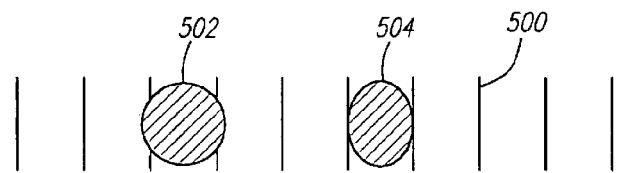
FIG. 24
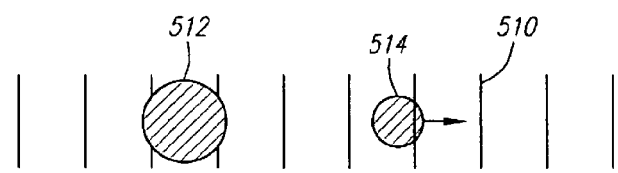
FIG. 25
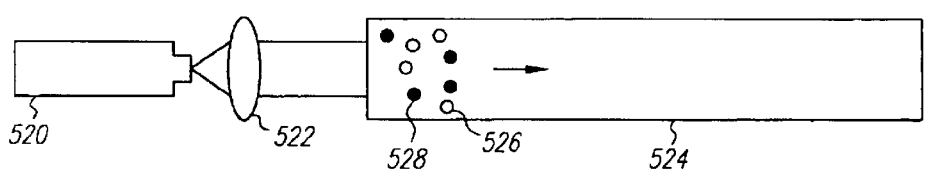
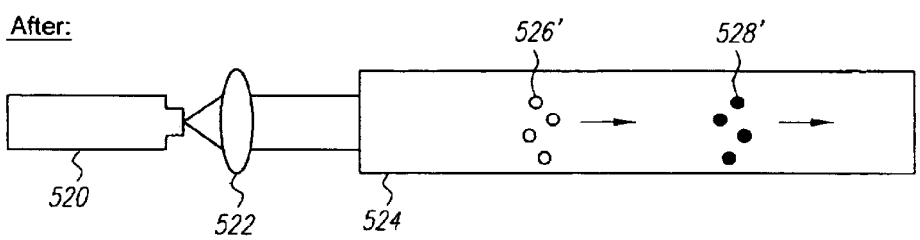
FIG. 26

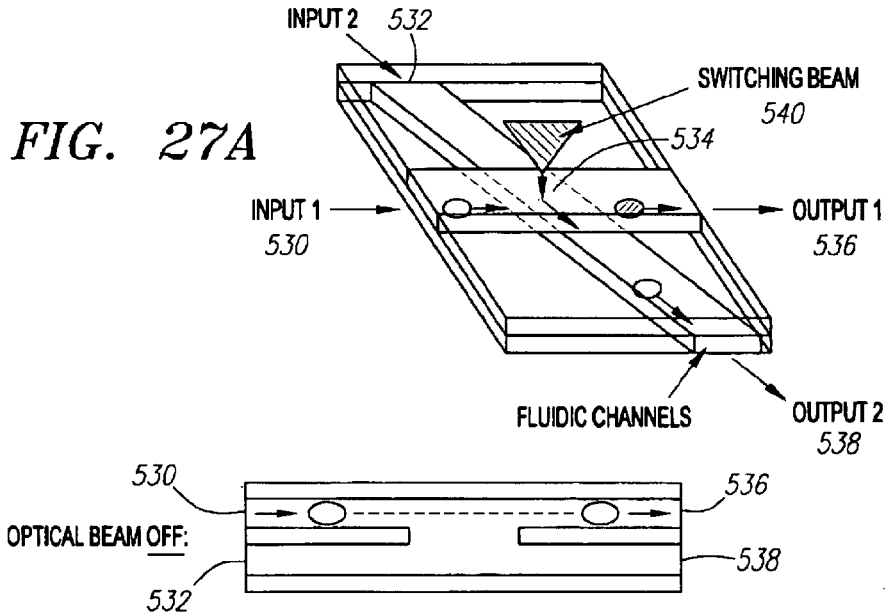
FIG. 27A
FIG. 27B
FIG. 27C
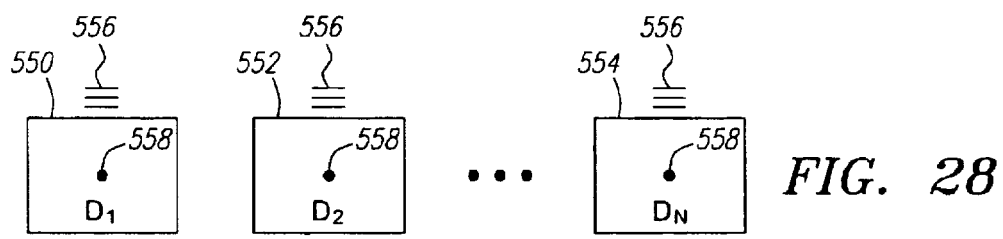
FIG. 28
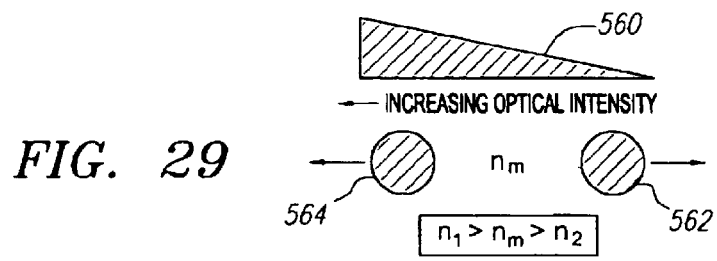
FIG. 29

Before　　　　　　　After　　　　　　　Difference

METHOD FOR SORTING PARTICLES

RELATED APPLICATIONS

This application is a continuation-in-part of Application Serial No. 09/845,245, filed Apr. 27, 2001, entitled "Methods and Apparatus for Use of Optical Forces for Identification, Characterization and/or Sorting of Particles".

This application is related to Application Serial No. 09/843,902, filed on Apr. 27, 2001, entitled "Method for Separating Micro-Particl s", as amended, with named inventor Osman Kibar, which claims priority from provisional Application Serial No. 60/248,451, entitled "Method and Apparatus for Sorting Cells or Particles", filed Nov. 13, 2000. Those applications are incorporated herein by reference as if fully set forth herein.

FIELD OF THE INVENTION

This invention relates to methods and apparatus for the selection, identification, characterization, and/or sorting of materials utilizing at least optical or photonic forces. More particularly, the inventions find utility in biological systems, generally considered to be the use of optical forces for interaction with bioparticles having an optical dielectric constant.

BACKGROUND OF THE INVENTION

Separation and characterization of particles has a wide variety of applications ranging from industrial applications, to biological applications, to environmental applications. For example, in the field of biology, the separation of cells has numerous applications in medicine and biotechnology. Historically, sorting technologies focused on gross physical characteristics, such as particle size or density, or to utilize some affinity interaction, such as receptor-ligand interactions or reactions with immunologic targets.

Electromagnetic response properties of materials have been utilized for particle sorting and characterization. For example, dielectrophoretic separators utilize non-uniform DC or AC electric fields for separation of particles. See, e.g., U.S. Pat. No. 5,814,200, Pethig et al., entitled "Apparatus for Separating By Dielectrophoresis". The application of dielectrophoresis to cell sorting has been attempted. In Becker (with Gascoyne) et al., PNAS USA, Vol. 92, pp. 860–864, January 1995, Cell Biology, in the article entitled "Separation of Human Breast Cancer Cells from Blood by Differential Dielectric Affinity", the authors reported that the dielectric properties of diseased cells differed sufficiently to enable separation of the cancer cells from normal blood cells. The system balanced hydrodynamic and dielectrophoretic forces acting on cells within a dielectric affinity column containing a microelectrode array. More sophisticated separation systems have been implemented. See, e.g., Cheng, et al., U.S. Pat. No. 6,071,394, "Channel-Less Separation of Bioparticles on a Bioelectronic Chip by Dielectrophoresis". Yet others have attempted to use electrostatic forces for separation of particles. See, e.g., Judy et al., U.S. Pat. No. 4,440,638, entitled "Surface Field-Effect Device for Manipulation of Charged Species", and Washizu "Electrostatic Manipulation of Biological Objects", Journal of Electrostatics, Vol. 25, No. 1, June 1990, pp. 109–103.

Light has been used to sort and trap particles. One of the earliest workers in the field was Arthur Ashkin at Bell Laboratories, who used a laser for manipulating transparent, μm-size latex beads. Ashkin's U.S. Pat. No. 3,808,550 entitled "Apparatuses for Trapping and Accelerating Neutral Particles" disclosed systems for trapping or containing particles through radiation pressure. Lasers generating coherent optical radiation were the preferred source of optical pressure. The use of optical radiation to trap small particles grew within the Ashkin Bell Labs group to the point that ultimately the Nobel Prize was awarded to researchers from that lab, including Steven Chu. See, e.g., Chu, S., "Laser Trapping of Neutral Particles", Sci. Am., p. 71 (February 1992), Chu, S., "Laser Manipulation of Atoms and Particles", Science 253, pp. 861–866 (1991).

Generally, the interaction of a focused beam of light with dielectric particles or matter falls into the broad categories of a gradient force and a scattering force. The gradient force tends to pull materials with higher relative dielectric constants toward the areas of highest intensity in the focused beam of light. The scattering force is the result of momentum transfer from the beam of light to the material, and is generally in the same direction as the beam. The use of light to trap particles is also sometimes referred to as an optical tweezer arrangement. Generally, utilizing the Rayleigh approximation, the force of trapping is given by the following equation:

$$F_g = 2\pi \cdot r^3 \frac{\sqrt{\varepsilon_B}}{c} \left(\frac{\varepsilon - \varepsilon_B}{\varepsilon + 2\varepsilon_B}\right)(\nabla \cdot I)$$

where $F_g$ is the optical gradient force on the particle in the direction toward the higher intensity, r is the radius of the particle, $\varepsilon_B$ is the dielectric constant of the background medium, $\varepsilon$ is the dielectric constant of the particle, I is the light intensity in watts per square centimeter and $\nabla$ is the spatial derivative. FIG. 1 shows a drawing of a particle in an optical tweezer. The optical tweezer consists of a highly focused beam directed to the particle.

As shown in FIG. 1, the focused beam 12 first converges on the particle 10 and then diverges. The intensity pattern 14 relates to the cross-section of the intensity of the beam in the horizontal dimension, and the intensity pattern 16 is the cross-section of intensity in the vertical dimension. As can be seen from the equation, the trapping force is a function of the gradient of the intensity of the light. Thus, the force is greater where the light intensity changes most rapidly, and contrarily, is at a minimum where the light intensity is uniform.

Early stable optical traps levitated particles with a vertical laser beam, balancing the upward scattering force against the downward gravitational force. The gradient force of the light served to keep the particle on the optical axis. See, e.g., Ashkin, "Optical Levitation by Radiation Pressure", Appl. Phys. Lett., 19(6), pp. 283–285 (1971). In 1986, Ashkin disclosed a trap based upon a highly focused laser beam, as opposed to light propagating along an axis. The highly focused beam results in a small point in space having an extremely high intensity. The extreme focusing causes a large gradient force to pull the dielectric particle toward that point. Under certain conditions, the gradient force overcomes the scattering force, which would otherwise push the particle in the direction of the light out of the focal point. Typically, to realize such a high level of focusing, the laser beam is directed through a high numerical aperture microscope objective. This arrangement serves to enhance the relative contribution from the high numerical aperture illumination but decreases the effect of the scattering force.

In 1987, Ashkin reported an experimental demonstration of optical trapping and manipulation of biological materials with a single beam gradient force optical trap system. Ashkin, et al., "Optical Trapping and Manipulation of Viruses and Bacteria", Science, 20 March, 1987, Vol. 235, No. 4795, pp. 1517–1520. In U.S. Pat. No. 4,893,886, Ashkin et al., entitled "Non-Destructive Optical Trap for Biological Particles and Method of Doing Same", reported successful trapping of biological particles in a single beam gradient force optical trap utilizing an infrared light source. The use of an infrared laser emitting coherent light in substantially infrared range of wavelengths, there stated to be 0.8 μm to 1.8 μm, was said to permit the biological materials to exhibit normal motility in continued reproductivity even after trapping for several life cycles in a laser power of 160 mW. The term "opticution" has become known in the art to refer to optic radiation killing biological materials.

The use of light to investigate biological materials has been utilized by a number of researchers. Internal cell manipulation in plant cells has been demonstrated. Ashkin, et al., PNAS USA, Vol. 86, 7914–7918 (1989). See also, the summary article by Ashkin, A., "Optical Trapping and Manipulation of Neutral Particles Using Lasers", PNAS USA, Vol. 94, pp. 4853–4860, May 1997, Physics. Various mechanical and force measurements have been made including the measurement of torsional compliance of bacterial flagella by twisting a bacterium about a tethered flagellum. Block, S., et al., Nature (London), 338, pp. 514–518 (1989). Micromanipulation of particles has been demonstrated. For example, the use of optical tweezers in combination with a microbeam technique of pulsed laser cutting, sometimes also referred to as laser scissors or scalpel, for cutting moving cells and organelles was demonstrated. Seeger, et al., Cytometry, 12, pp. 497–504 (1991). Optical tweezers and scissors have been used in all-optical in vitro fertilization. Tadir, Y., Human Reproduction, 6, pp. 1011–1016 (1991). Various techniques have included the use of "handles" wherein a structure is attached to a biological material to aid in the trapping. See, e.g., Block, Nature (London), 348, pp. 348–352 (1990).

Various measurements have been made of biological systems utilizing optical trapping and interferometric position monitoring with subnanometer resolution. Svoboda, Nature (London), 365, pp. 721–727 (1993). Yet others have proposed feedback based systems in which a tweezer trap is utilized. Molloy, et al., Biophys. J., 68, pp. 2985–3055 (1995).

A number of workers have sought to distort or stretch biological materials. Ashkin in Nature (London), 330 pp. 769–771 (1987), utilized optical tweezers to distort the shape of red blood cells. Multiple optical tweezers have been utilized to form an assay to measure the shape recovery time of red blood cells. Bronkhorst, Biophys. J., 69, pp. 1666–1673 (1995). Kas, et al., has proposed an "optical stretcher" in U.S. Pat. No. 6,067,859 which suggests the use of a tunable laser to trap and deform cells between two counter-propagating beams generated by a laser. The system is utilized to detect single malignant cancer cells. Yet another assay proposed colliding two cells or particles under controlled conditions, termed the OPTCOL for optical collision. See, e.g., Mammer, Chem & Biol., 3, pp. 757,763 (1996).

Yet others have proposed utilizing optical forces to measure a property of an object. See, e.g., Guanming, Lai et al., "Determination of Spring Constant of Laser-Trapped Particle by Self-Mining Interferometry", Proc. of SPIE, 3921, pp. 197–204 (2000). Yet others have utilized the optical trapping force balanced against a fluidic drag force as a method to calibrate the force of an optical trap. These systems utilize the high degree of dependence on the drag force, particularly Stokes drag force.

Yet others have utilized light intensity patterns for positioning materials. In U.S. Pat. No. 5,245,466, Burnes et al., entitled "Optical Matter", arrays of extended crystalline and non-crystalline structures are created using light beams coupled to microscopic polarizable matter. The polarizable matter adopts the pattern of an applied, patterned light intensity distribution. See also, "Matter Rides on Ripples of Lights", reporting on the Burns work in New Scientist, Nov. 18, 1989, No. 1691. Yet others have proposed methods for depositing atoms on a substrate utilizing a standing wave optical pattern. The system may be utilized to produce an array of structures by translating the standing wave pattern. See, Celotta et al., U.S. Pat. No. 5,360,764, entitled "Method of Fabricating Laser Controlled Nanolithography".

Yet others have attempted to cause motion of particles by utilizing light. With a technique termed by its authors as "photophoresis", Brian Space, et al., utilized a polarized beam to induce rotary motion in molecules to induce translation of the molecules, the desired goal being to form a concentration gradient of the molecules. The technique preferably utilizes propeller shaped molecules, such that the induced rotary motion of the molecules results in translation.

Various attempts have been made to form microfluidic systems, put to various purposes, such as sample preparation and sorting applications. See, e.g., Ramsey, U.S. Pat. No. 6,033,546, entitled "Apparatus and Method for Performing Microfluidic Manipulations for Chemical Analysis and Synthesis". Numerous companies, such as Aclara and Caliper, are attempting to form micro-systems comprising a 'lab on a chip'.

Others have attempted to combine microfabricated devices with optical systems. In "A Microfabricated Device for Sizing and Sorting DNA Molecules", Chou, et al., PNAS USA, Vol. 96, pp. 11–13, January 1999, Applied Physical Sciences, Biophysics, a microfabricated device is described for sizing and sorting microscopic objects based upon a measurement of fluorescent properties. The paper describes a system for determining the length of DNA by measuring the fluorescent properties, including the amount of intercalated fluorescent dye within the DNA. In "A Microfabricated Fluorescence-Activated Cells Sorter", Nature Biotechnology, Vol. 17, November 1999, pp. 1109–1111, a "T" microfabricated structure was used for cell sorting. The system utilized a detection window upstream of the "T" intersection and based upon the detected property, would sort particles within the system. A forward sorting system switched fluid flow based upon a detected event. In a reverse sorting mode, the fluid flow was set to route all particles to a waste collection, but upon detection of a collectible event, reversed the fluid flow until the particle was detected a second time, after which the particle was collected. Certain of these systems are described in Quake et al., PCT Publication WO 99/61888, entitled "Microfabricated Cell Sorter".

Yet others have attempted to characterize biological systems based upon measuring various properties, including electromagnetic radiation related properties. Various efforts to explore dielectric properties of materials, especially biological materials, in the microwave range have been made. See, e.g., Larson et al., U.S. Pat. No. 4,247,815, entitled "Method and Apparatus for Physiologic Facsimile Imaging of Biologic Targets Based on Complex Permittivity Measurements Using Remote Microwave Interrogation", and PCT Publication WO 99/39190, named inventor Hefti, entitled "Method and Apparatus for Detecting Molecular Binding Events".

Despite the substantial effort made in the art, no comprehensive, effective, sensitive and reliable system has been achieved.

SUMMARY OF THE INVENTION

The methods and apparatus of this relate generally to the use of light energy to obtain information from, or to apply forces to, particles. The particles may be of any form which have a dielectric constant. The use of light for these beneficial purposes is the field of optophoresis. A particle, such as a cell, will have a Optophoretic constant or signature which is indicative of a state, or permits the selection, sorting, characterization or unique interaction with the particle. In the biological regime, the particles may include cells, organelles, proteins, or any component down to the atomic level. The techniques also apply in the non-biological realm, including when applied to all inorganic matter, metals, semiconductors, insulators, polymers and other inorganic matter.

Considering the biological realm, the cell represents the true point of integration for all genomic information. Accessing and deciphering this information is important to the diagnosis and treatment of disease. Existing technologies cannot efficiently and comprehensively address the enormous complexity of this information. By unlocking the fundamental properties of the cell itself, the methods and apparatus described herein create new parameters for cellular characterization, cellular analysis and cell-based assays.

This technology represents a practical approach to probing the inner workings of a particle, such as a living cell, preferably without any dyes, labels or other markers. The "Optophoretic Constant" of a cell uniquely reflects the physiological state of the cell at the exact moment in which it is being analyzed, and permits investigation of the inner workings of cells. These techniques allow simple and efficient gathering of a wide spectrum of information, from screening new drugs, to studying the expression of novel genes, to creating new diagnostic products, and even to monitoring cancer patients. This technology permits the simultaneous analysis and isolation of specific cells based on this unique optophoretic parameter. Stated otherwise, this technology is capable of simultaneously analyzing and isolating specific particles, e.g. cells, based on their differences at the atomic level. Used alone or in combination with modern molecular techniques, the technology provides a useful way to link the intricate mechanisms involving the living cell's overall activity with uniquely identifiable parameters.

In one aspect, the invention is a method for the characterization of a particle by the steps of observing a first physical position of a particle, optically illuminating the particle to subject it to an optical force, observing the second physical position of the particle, and characterizing the particle based at least in part upon reaction of the particle to the optical force. The characterization may be that the particle, e.g., a cell, has a certain disease state based upon the detected optophoretic constant or signature.

While characterization may be done with or without physical separation of multiple particles, a method for separating particles may consist of, first, subjecting particles to optical gradient force, second, moving the particle, and third, separating desired particle from other particles. The particle may be separate from the others by further optical forces, by fluidic forces, by electromagnetic forces or any other force sufficient to cause the required separation. Separation may include segregation and sorting of particles.

In yet another aspect, the invention includes a method for analyzing particles by electrokinetically moving the particles, and subjecting the particles to optical forces for sorting. The electrokinetic forces may include, for example, eletroosmosis, electrophoresis and dielectrophoresis.

In addition to the use of the dielectric aspects of the particle for characterization and sorting, certain of the inventive methods may be used to determine the dielectric constant of a particle. One method consists of subjecting the particle to an optical gradient force in a plurality of media having different dielectric constants, monitoring the motion of the particle when subject to the optical gradient force in the various media, and determining the dielectric constant of the particle based upon the relative amount of motion in the various media.

Yet other methods permit the sorting of particles according to their size. One method includes the steps of subjecting the particles to a optical fringe pattern, moving the fringes relative to the particles, wherein the improvement comprises selecting the period of the fringes to have a differential effect on differently sized particles. An allied method sorts or otherwise separates particles based upon the particles flexibility when subject to a optical force. One set of exemplary steps includes: subjecting the particles to an optical pattern having fringes, the fringe spacing being less than the size of the particle in an uncompressed state, moving the fringes relative to the medium containing the particles, and whereby particles having relatively higher flexibility are separated from those with relatively lower flexibility.

In addition to the use of optical gradient forces, the systems and methods may use, either alone or in combination with other forces, the optical scattering force. One method for separation in an optophoresis set up consists of providing one or more particles, subjecting the particles to light so as to cause a scattering force on the particles, and separating the particles based upon the reaction to at least the scattering force.

Various techniques are described for enhancing the sensitivity and discrimination of the system. For example, a sensitive arrangement may be provided by separating the particles in a medium having a dielectric constant chosen to enhance the sensitivity of the discrimination between the particles, and changing the medium to one having a dielectric constant which causes faster separation between the particles. One option for enhancing the sensitivity is to choose the dielectric constant of the medium to be close to the dielectric constant of the particles.

Accordingly, it is an object of this invention to provide a method of identification, characterization, selection and/or sorting of materials having an optical dielectric constant.

It is yet a further object of this invention to provide a system for sorting or identifying particles without labeling or otherwise modifying the particle.

It is yet another object of this invention to provide a system in which uncharged or neutral particles may be sorted or otherwise characterized.

Yet another object of this invention is to provide a system in which particles may be manipulated remotely, thereby reducing the contamination to the system under study.

It is yet another object of this invention to provide a system for characterizing, moving and/or sorting particles that may be used in conjunction with other forces, without interference between the optical forces and the other forces.

BRIEF DESCRIPTION OF THE DRAWINGS

FIG. 1 is a graphical depiction of optical intensity patterns for a prior art optical tweezer system, showing both the focus beam, a particle and the cross-section of intensity of the beam.

FIGS. 14A and 14B show graphical depictions of particle sorting from a one-dimensional particle source, in FIG. 14A showing the particle flow and in FIG. 14B showing particles transported in a fluid flow.

FIG. 15 is a plan view drawing of a "T" channel sorting structure.

FIG. 16 is a plan view of an "H" sorting structure.

FIG. 17 is a plan view of a "Y" shaped sorting structure.

FIG. 18 is a plan view of a "X" channel sorting structure.

FIG. 24 is a plan view of a particle analysis system utilizing particle deformability as a factor in the selection or characterization.

FIG. 25 is a plan view of a sorting or characterization system utilizing the particle size relative to the optical gradient periodicity as a factor.

FIG. 26 is a system for separation of particles utilizing the scattering force of light for separation.

FIG. 27A is a perspective drawing of a scattering force switch.

FIG. 27B is a plan, side view of a scattering force switch.

FIG. 27C is a plan, side view of a scattering force switch with the beam on.

FIG. 28 is a schematic drawing of a system for determining the dielectric constant of particles in various fluidic media of varying dielectric constant.

FIG. 29 is a cross-sectional drawing of particles and a light intensity profile for separating particles in a dielectric medium.

DETAILED DESCRIPTION OF THE INVENTION

Definitions

Figure 2:
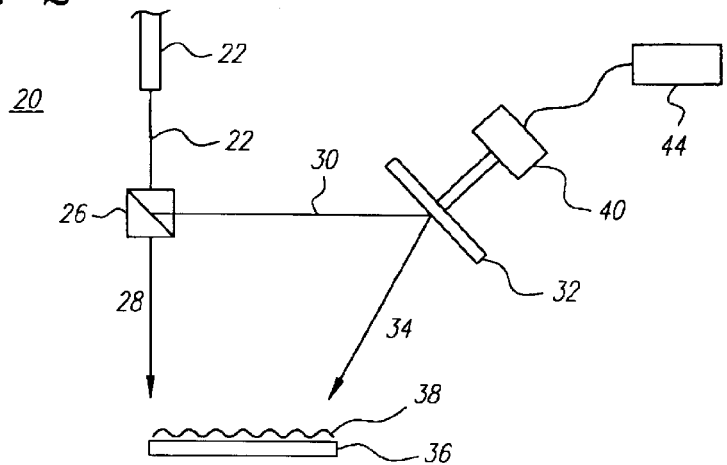
FIG. 2 is a cross-sectional drawing of the optical system for interfering two beams utilizing a variable path length by moving a mirror.

The following definitions are provided for an understanding of the invention disclosed herein.

"Dielectric constant" is defined to be that property which determines the electrostatic energy stored per unit volume for unit potential gradient. (See, e.g., the New IEEE Standard Dictionary Of Electrical And Electronics Terms, ©1993).

The "optical dielectric constant" is the dielectric constant of a particle or thing at optical wavelengths. Generally, the optical wavelength range is from 150 Å to 30,000 Å.

An "optical gradient field" is an optical pattern having a variation in one or more parameters including intensity, wavelength or frequency, phase, polarization or other parameters relating to the optical energy. When generated by an interferometer, an optical gradient field or pattern may also be called an optical fringe field or fringe pattern, or variants thereof.

A "moving optical gradient field" is an optical gradient field that moves in space and/or time relative to other components of the system, e.g., particles or objects to be identified, characterized, selected and/or sorted, the medium, typically a fluidic medium, in contact with the particles, and/or any containment or support structure.

An "optical scattering force" is that force applied to a particle or thing caused by a momentum transfer from photons to material irradiated with optical energy.

An "optical gradient force" is one which causes a particle or object to be subject to a force based upon a difference in dielectric constant between the particle and the medium in which it is located.

"Optophoresis" or "Optophoretic" generally relates to the use of photonic or light energy to obtain information about or spatially move or otherwise usefully interact with a particle.

"Optophoretic constant" or "optophoretic signature" or "optophoretic fingerprint" refer to the parameter or parameters which distinguish or characterize particles for optical selection, identification, characterization or sorting.

An "optical tweezer" is a light based system having a highly focused beam to a point in space of sufficiently high intensity that the gradient force tends to pull a dielectric particle toward the point of highest intensity, typically with the gradient force being sufficiently strong to overcome the scattering force. Most typically, the laser beam is directed through a microscope objective with a high numerical aperture, with the beam having a diffraction limited spot size of approximately the wavelength of the light, 5,000 to 20,000 Å, though more typically 10,000 Å. Generally, an optical tweezer has a beam width in the focal plane of 2 $\mu$m or less, and typically about 1 $\mu$m.

"Separation" of two objects is the relative spatial distancing over time of a particle from some other reference point or thing.

"Sorting" involves the separation of two or more particles in a meaningful way.

DESCRIPTION OF EXEMPLARY APPARATUS

Optical Components—Generation of Moving Optical Gradient Field

FIGS. 2–10 describe various systems for generation of optical patterns, sometimes termed fringe patterns or optical fringe patterns, including, but not limited to, a moving optical gradient field pattern. These exemplary embodiments are intended to be illustrative, and not limiting, as other apparatus may be utilized to generate the optical fields and forces to achieve the desirable results of these inventions.

The points raised in discussions of specific embodiments may be considered to be generally applicable to descriptions of the other embodiments, even if not expressly stated to be applicable.

The light source for use with systems has certain generally desirable properties. As to wavelength, the wavelength will generally be chosen based upon one or more considerations. In certain applications, it may be desirable to avoid damage to biological materials, such as cells. By choosing wavelengths in ranges where the absorption by cellular components, mostly water, are minimized, the deleterious effects of heating may be minimized. Wavelengths in the range from approximately 0.3 $\mu$m to approximately 1.8 $\mu$m, and more preferably, from substantially 0.8 to substantially 1.8 $\mu$m, aid in reducing biological damage. However, even for biological applications, a laser having a wavelength generally considered to be damaging to biological materials may be used, such as where the illumination is for a short period of time where deleterious absorption of energy does not occur. In yet other applications, it may be desirable to choose a wavelength based upon a property of the particle or object under consideration. For example, it may be desirable to choose the wavelength to be at or near an absorption band in order to increase (or decrease) the force applied against a particle having a particular attribute. Yet another consideration for wavelength choice may be compatibility with existing technology, or a wavelength naturally generated by a source. One example would be the choice of the wavelength at 1.55 $\mu$m. Numerous devices in the 1.55 $\mu$m wavelength region exist commercially and are used extensively for telecommunications applications.

Generally, the light sources will be coherent light sources. Most typically, the coherent light source will consist of a laser. However, non-coherent sources may be utilized, provided the system can generate the forces required to achieve the desired results. Various laser modes may be utilized, such as the Laguerre-Gaussian mode of the laser. Furthermore, if there is more than one light source in the system, these sources can be coherent or incoherent with respect to each other.

The spot size or periodicity of the intensity pattern is preferably chosen to optimize the effective results of the illumination. In many applications, it is desirable to have a substantially uniform gradient over the particle, e.g., cell, to be interrogated such that the dielectric properties of the entire particle (cell) contribute to the resulting force. Broadly, the range varies from substantially 1 to substantially 8 times the size (diameter or average size) of the particle or object, more preferably, the range is from substantially 2 to substantially 4 times the size. Various methods and systems known to those skilled in the art may be utilized to achieve the desired spot size or periodicity, e.g., using a defocused beam or a collimated beam having the desired size. The typical characterization of the radius of the spot is the 1/$e^2$ radius of the beam intensity. For many applications, including cellular applications, the beam size will be on the order of 10 microns, though sometimes as small as five microns, and in even certain other occasions, as small as two microns. In certain applications, it is desirable to have the periodicity of the illumination in the range from substantially 1 to substantially 2 times the size (diameter or average size) of the particle or object. For many biological applications, a periodicity of from substantially 5 $\mu$m to 25 $\mu$m, and more preferably from 10 $\mu$m to 20 $\mu$m. Certain applications may utilize smaller sizes, e.g., for bacteria, or larger sizes, e.g., for larger particles. In yet other applications, it may be desired to utilize a spot size smaller than the particle or object, such as where interrogation of a sub-cellular region is desired.

The examples of systems for generating intensity patterns, described below, as well as other systems for generating intensity patterns useful for the subject inventions include various optical components, as well as a control system to generate the desired pattern, intensity profile or other gradient, such as a moving optical field gradient. Various optical systems may be adapted for use in the systems of the invention, so as to effectively carry out the methods and achieve the results described herein. Exemplary systems which may be adapted in whole or in part include: Young's slits, Michelson interferometer, Mach-Zender interferometer, Haidinger circular fringe systems, Fresnel mirror interferometer, plane-parallel plate interferometer, Fabry-Perot interferometer and any other system for generating an optical gradient intensity pattern or fringe pattern.

Turning now to a detailed description of exemplary systems for use with the subject inventions. FIG. 2 shows an optical component description of a system 20 generally configured to generate a moving optical gradient field pattern to provide a force on one or more particles provided to the system 20. The optical forces may then be used for characterization, identification, selection and/or sorting of the particles. A light source 22, preferably a laser, generates a first beam 24 directed toward beam splitter 26. Beam splitter 26 may be of any mode or type known to the art, such as a prism beam splitter, consistent with the goals and objects of this invention. A first transmitted beam 28 passes through the beam splitter 26. A first reflected beam 30 reflects from the beam splitter 26 to a reflective surface 32, typically a mirror, to generate a second reflected beam 34. The first transmitted beam 28 and second reflected beam 34 interfere and generate an intensity pattern 38, generally being located at the operative portion of the slide or support 36 where the light would interact with the particle or object of interest. The optical pattern 38 moves relative to other objects, e.g., the particles, the substrate, and/or the fluidic medium containing the particles, by virtue of a change in the optical path length between the first transmitted beam 28 and the combination of the first reflected beam 30 and second reflected beam 34. Mirror 32 is movable, by actuator 40. One example of an actuator 40 could comprise a motor and screw system to move mirror 32. Numerous alternative structures for moving mirror 32 are known to the art, e.g., piezoelectric systems, oscillating mirror systems and the like.

Figure 3:
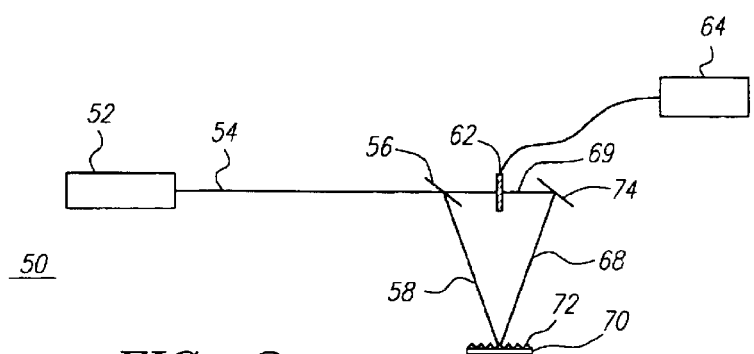
FIG. 3 is a schematic diagram of a system utilizing interference between two beams where the path length is varied utilizing a phase modulator.

FIG. 3 shows a two-beam interference based system. A source of coherent light, such as laser 52, generates a first beam 54 directed to a beam splitter 56. A first reflected beam 58 is directed toward the sample plate 70 and a first transmitted beam 60 is directed to a modulator, such as a phase modulator 62. The phase modulator 62 may be of any type known to those skilled in the art. Phase modulator 62 is under control of the control system 64 and results in modulated beam output 66 which is directed to a mirror 74. The modulated beam 66 reflects from mirror 74 to generate the second reflected beam 68 which is directed to the sample plate 70. The first reflected beam 54 and second reflected beam 68 generate a pattern 72 at the operative interface with the sample plate 70. The control system 64 is connected to the phase modulator 62 so as to cause the pattern 72 to move relative to the objects within the system 50, such as the sample plate 70.

Figure 4:
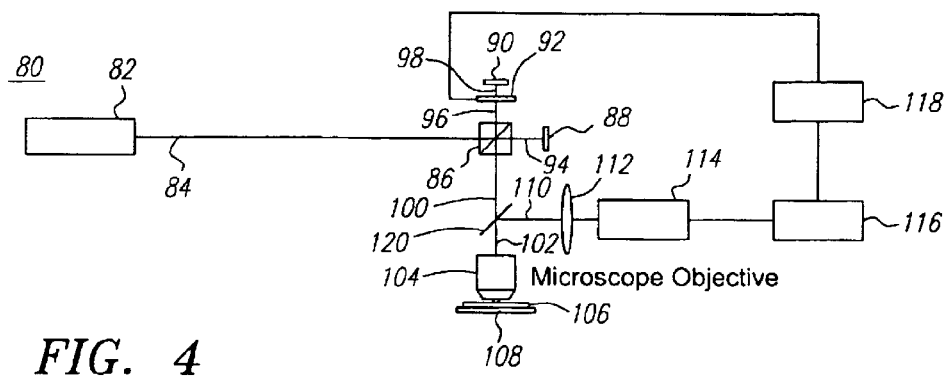
FIG. 4 is a cross-sectional drawing of an optical system utilizing an interferometer where the path length is adjustable via a phase modulator.

FIG. 4 shows an optical component diagram of an interferometer system 80. A light source, such as laser 82, generates a first light beam 84 directed to beam splitter 86. An interferometer composed of the first mirror 88 and second mirror 90 generate an output beam 100 having the desired beam properties, including the desired gradient properties. The first beam 84 passes through beam splitter 86 to generate a first transmitted beam 94 directed to first mirror 88. The reflected beam retraces path 94 to the beam splitter 86. The first reflected beam 96 passes through phase modulator 92 to generate first modulated beam 98 directed to the second mirror 90. The reflected beam from second mirror 90 retraces the path 98 through the phase modulator 92 and beam 96 to the beam splitter 86. The beam 100 is output from the interferometer section of the system 80 and directed toward the microscope objective 104.

The objective 104 is directed toward the sample plate 106. Optionally, a mirror 108, most preferably a planar mirror, may be disposed beneath the sample plate 106. The mirror 108 is oriented so as to provide reflected light onto the sample plate 106 bearing or containing the particles or objects under analysis or action of the system 80. The scattering force caused by the beam 102 as initially illuminates the sample plate 106 may be counteracted, in whole or in part, by directing the reflected radiation from mirror 108 back toward the sample. As discussed more in the section relating to surface effects, below, the reflected light and the upward scattering force reduce the overall effects of the scattering forces, such that the gradient forces may be more effectively utilized.

FIG. 4 includes an optional imaging system. The light 102 from the objective 104 is reflected by the beam splitter 120 generating third reflected beam 110 which is directed toward imaging optics 112. The optics 112 image the light on a detector 114, such as a charge couple device (CCD) detector. The output of the detector 114 may be provided to an imaging system 116. The imaging system 116 may optionally include a display, such as a monitor (CRT, flat panel display, plasma display, liquid crystal display, or other displays known to those skilled in the art). The imaging system 116 may optionally include image enhancement software and image analysis software, recording capability (to tape, to optical memory, or to any other form of memory known to those skilled in the art).

A control system 118 controls the modulator 92 so as to generate the desired optical force pattern within the system 80. Optionally, the imaging system 116 may be coupled to the control system 118. A feedback system may be created whereby the action of the particles on the sample plate 106 may be imaged through the system 116 and then utilized in the control system analysis to control the operation of the overall system 80.

Figure 5:
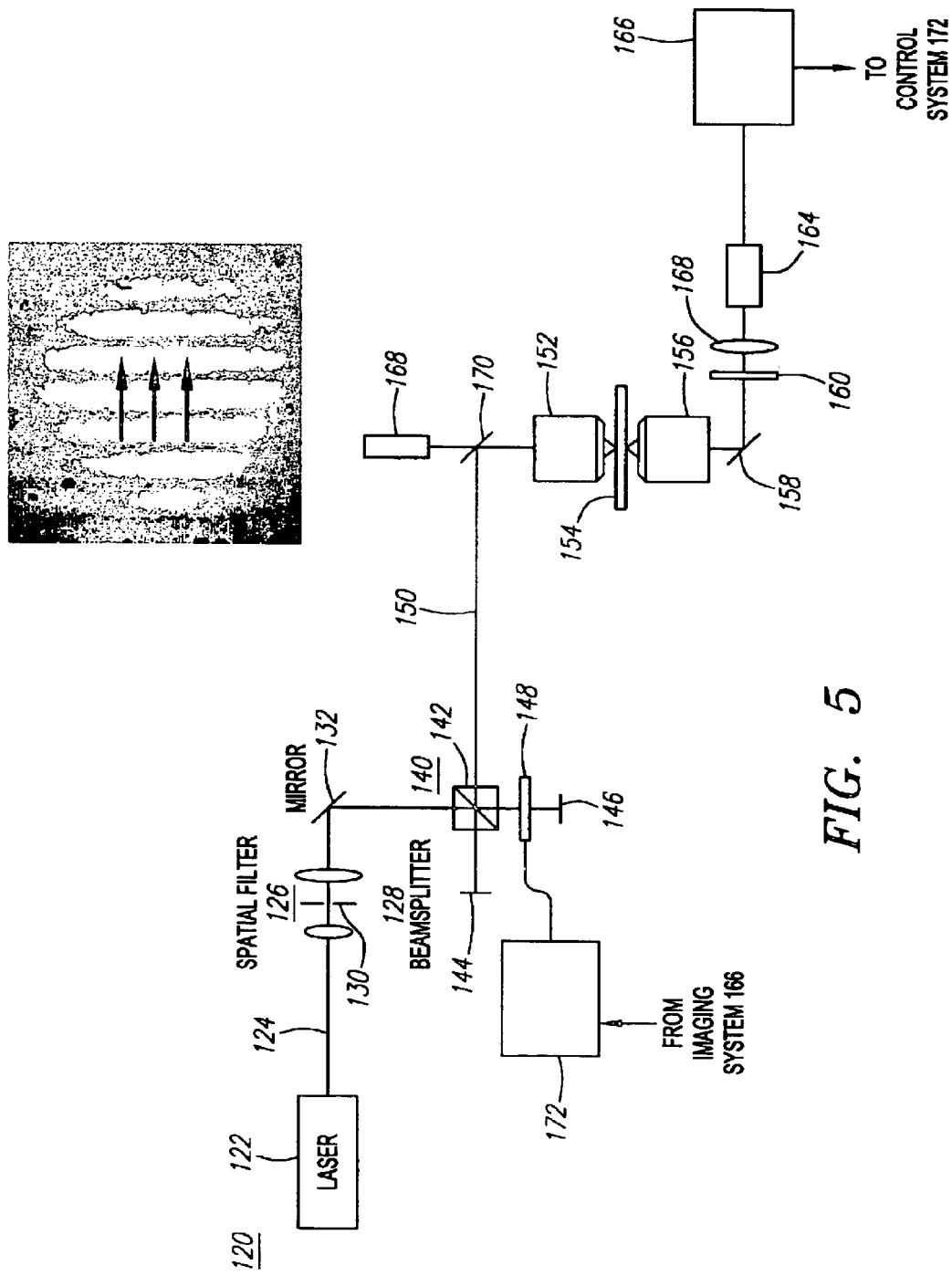
FIG. 5 is a cross-sectional drawing of an optical system including an interferometer and a phase modulator for changing the optical path length, and includes a photograph of a wave pattern generated by the system.

FIG. 5 shows a interferometer based system 120. A light source, such as laser 122, generates a first beam 124 directed toward an optional spatial filter 126. The spatial filter 126 would typically include lenses 128 and a spatial filter aperture 130. The aperture typically is round. The spatial filters serves to collimate the laser beam and to produce a smooth intensity profile across the wavefront of the laser beam. The interferometer 140 includes first mirror 146 and second mirror 144, as well a beam splitter 142. The phase modulator 148 is disposed within one of the two arms of the interferometer 140.

As shown in FIG. 5, a mirror 132 is optionally disposed to reflect the light from the source 122 to the interferometer 140. As will be appreciated by those skilled in the art, optical systems may include any number or manner of components designed to transfer or direct light throughout the system. One such example is the planar mirror 132 which merely serves to direct the radiation from one major component, e.g., the spatial filter, to another major component, e.g., the interferometer 140. In addition to mirrors, other common transfer components may include fiber optics, lenses, beam splitters, diffusers, prisms, filters, and shaped mirrors.

Beam 150 exits the interferometer 140 and is directed toward objective 152 and imaged at or near the sample plate 154. As shown, a dichroic mirror 170 serves to reflect the light 150, but to also permit passage of light from source 168, such as a fiber providing radiation from a source through the dichroic mirror 170 and objective 152 to illuminate the operative regions of the sample plate 154.

Optionally, a detection system may be disposed to image the operative portions of the sample plate 154. As shown, objective 156 is disposed beneath the sample plate 154, with the output radiation being transferred via mirror 158 to an imaging apparatus 164, such as a charge couple device (CCD). Optionally, an infrared filter 160 may be disposed within the optical path in order to select the desired wavelengths for detection. The output of the detector 164 is provided to an imaging system 166. As described in connection with other figures, the imaging system 166 may include image enhancement and image analysis software and provide various modes of display to be user. Optionally, the imaging system 166 is coupled to the control system 172 such as when used for feedback.

Figure 6:
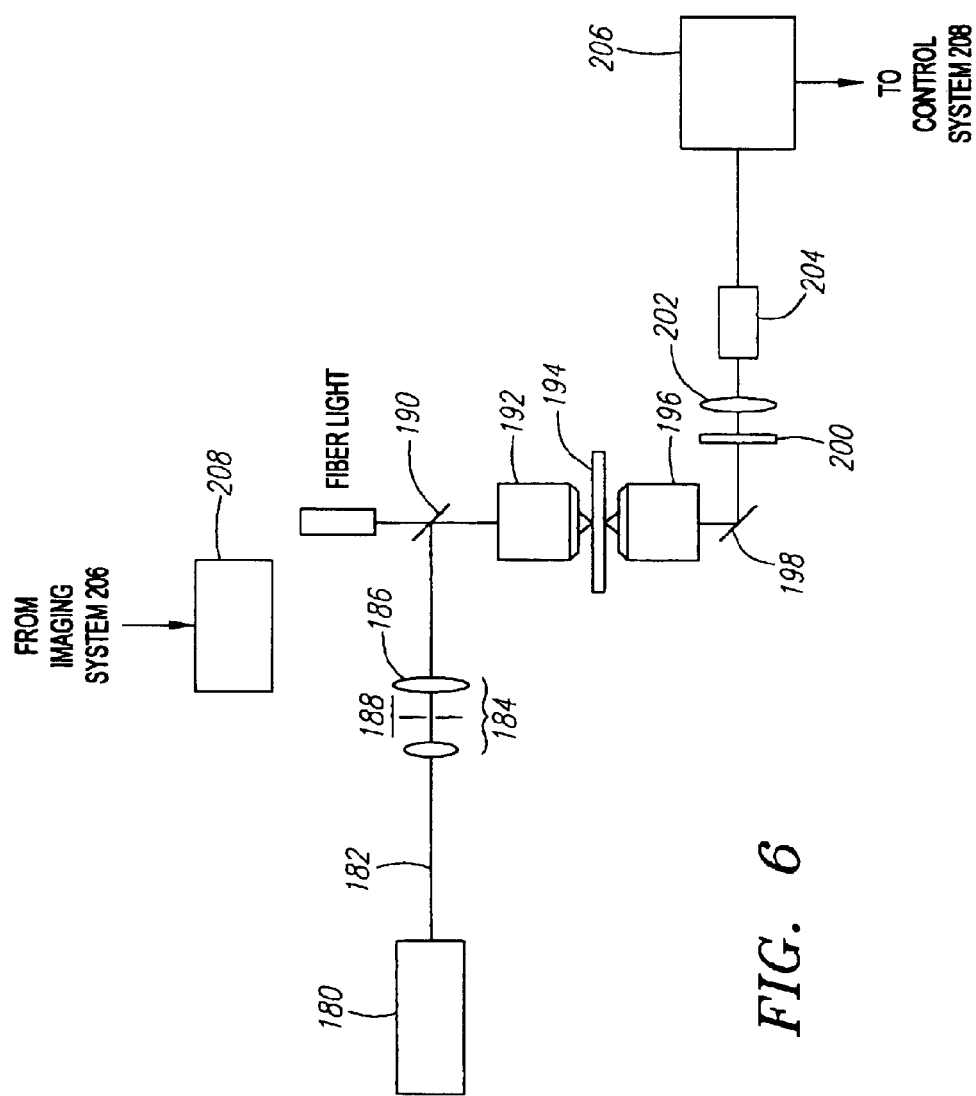
FIG. 6 is a cross-sectional drawing of an optical system utilizing separate illumination and imaging systems.

FIG. 6 shows an optical system having illumination of a sample plate 194 from the top side and imaging from the bottom side. A laser 180 generates a first beam 182 which optionally passes through a spatial filter 184. The spatial filter as shown includes lens 184 and aperture 188. The output of the spatial filter 184 passes through the objective 192 and is imaged onto the sample plate 194. The sample plate 194 and material supported on it may be imaged via an objective 196. An optional mirror 198 directs radiation to an optional filter 200 through an imaging lens 202 onto the detector 204. The detector 204 is coupled to an imaging system 206. Preferably, the imaging system 206 provides information to a control system 208 which controls various optical components of the system.

Figure 7:
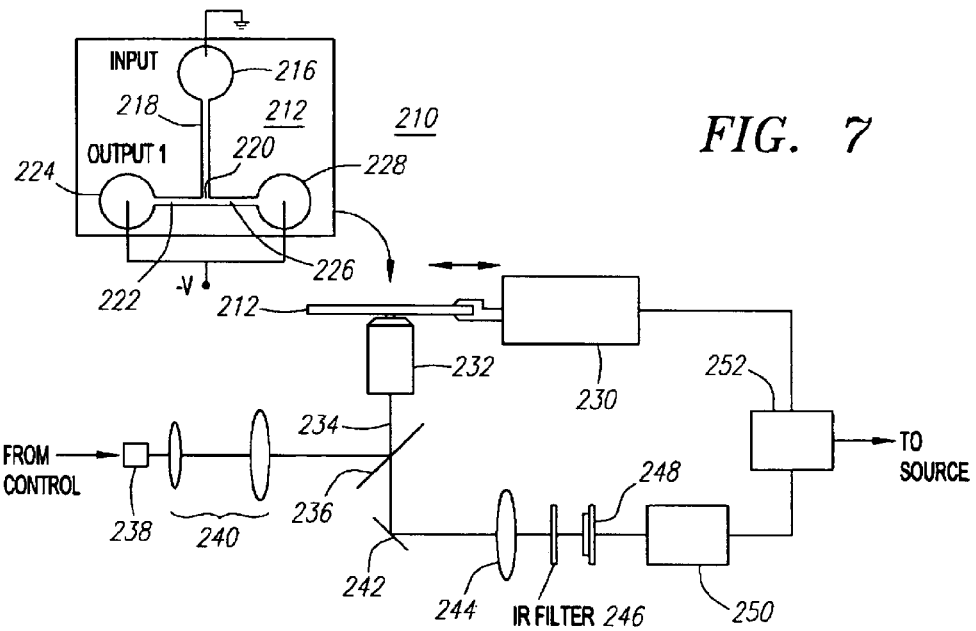
FIG. 7 is a depiction of an optical system interfacing with a fluidic system.

FIG. 7 shows an optical system interfacing a sample plate which includes bounded structures. The system 210 includes a sample plate 212 which optionally includes microfluidic channels. Alternatively, the sample plate 212 may support a separate structure containing the microfluidic channels. As one exemplary structure formed from the microfluidic channels, a "T" sorting arrangement is shown for a simple, though useful, example. An input reservoir 216 connects to a first channel 218 which terminates in a T at intersection 220. A first output channel 222 couples to a first output reservoir 224. A second output channel 226 couples to a second output chamber 228. As shown, the input chamber is coupled to ground and the first output chamber 224 and second output chamber 228 are connected to −V. The fluidic channel structures are discussed in more detail, below.

The microscope objective 232 serves to both provide the optical radiation to the sample plate 222 as well as to provide the imaging of the system. A light source 238, such as a laser, or more particularly, a laser diode, generates light which may be imaged by optics 240. A dichroic beam splitter 236 directs the radiation to the microscope objective 232. As shown, the objective has a magnification power of 100. For the biological applications, a magnification range of from 1 to 200 is desired, and more preferably, from 10 to 100. The objective 232 has a 1.25 numerical aperture. The preferable range of numerical apertures for the lenses is from 0.1 to 1.50, and more preferably from 0.4 to 1.25. The output from the objective 232 passes through the beam splitter 236, reflects from optional mirror 242 through optics (e.g., lens) 244, through the optional filter 246 to the imaging device 280. The imaging device, shown as a CCD, is connected to the imaging system 282. The output of the imaging system 282 is optionally coupled to the control system 284. As shown, the control system 284 controls both the translation stage 232 connected to the sample plate 212, as well as to the light source 238.

Figure 8:
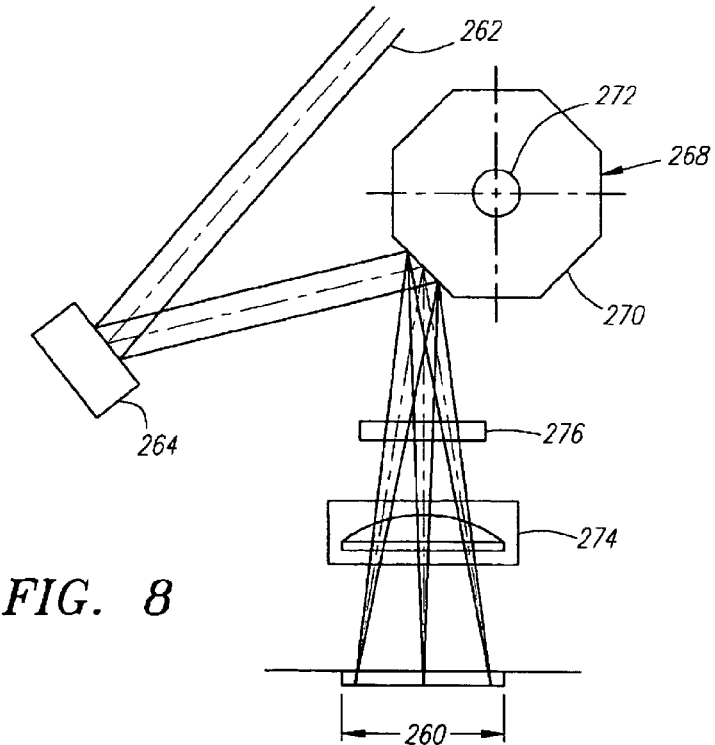
FIG. 8 is a cross-sectional drawing of an optical system utilizing a moving scanning system.

FIG. 8 shows a system for generating an intensity pattern within the scanned area 260. An input beam 262, such as from a coherent light source, such as a laser, is directed toward the system. A first oscillating component 264, such as a galvanometer or resonant scanner, intercepts the input beam 262 and provides a first degree of motion to the beam. The beam is directed to a polygonal mirror 268 which contains multiple faces 270. As the polygonal mirror 268 rotates around axis 272, the light is swept across the scanner area 260. Lens 274 are provided as required to appropriately image the light into the scanned area 260. Optionally, a mask or other pattern 276 may be disposed within the optical pathway so as to provide for the variation of the optical forces within the scanned area 260. Any of a wide variety of techniques for generating either the oscillatory motion or the scanning via the polygonal mirror are known to those skilled in the art.

Figure 9A:
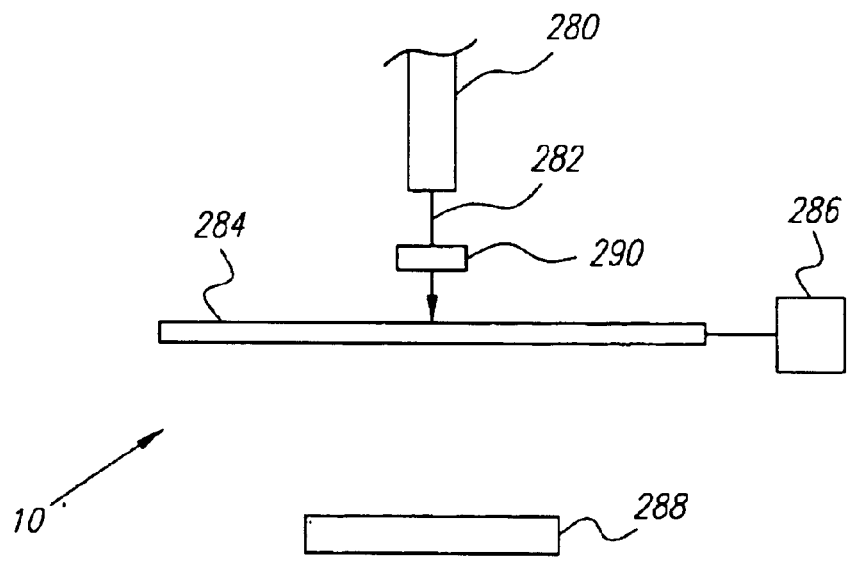
FIGS. 9A and 9B are cross-sectional drawings of an optical system including a mask based generation of intensity pattern.
Figure 9B:
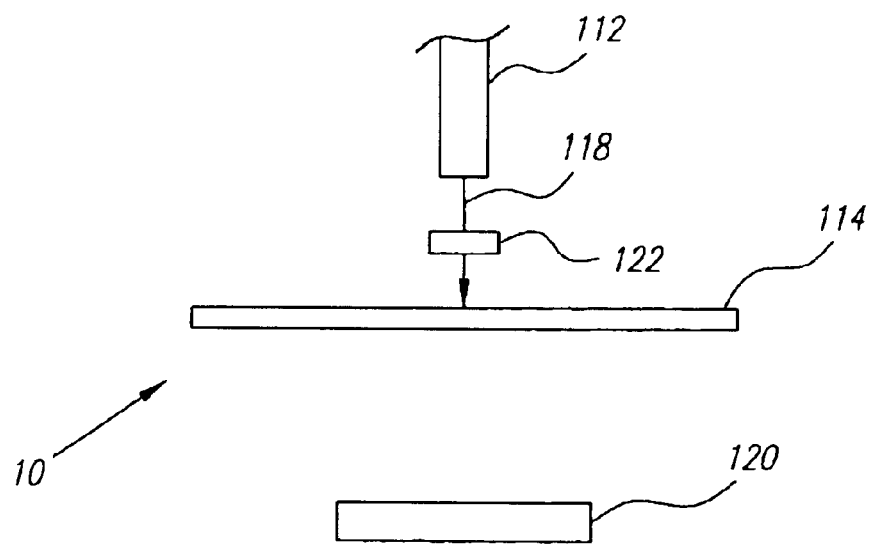

FIG. 9 shows a system utilizing masks to generate an optical force pattern. A source 280, such as a laser, generates a beam 282 directed to toward a mask 284. Optionally, a phase modulator 290 may be disposed between the source 280 and the mask 284. Optionally, the mask 284 may be moved, such as by actuator 286, which may be a motor, piezoelectric driven system, microelectromechanical (MEMs), or other driving structures known to those skilled in the art. The optical mask 284 creates a desired light intensity pattern adjacent the sample plate 288. The optical mask 284 may modulate any or all of the components of the light passing there through, include, but not limited to, intensity, phase and polarization. The mask 284 may be a holographic mask which, if used, may not necessarily require coherent light. Other forms of masks, such as spatial light modulators may be utilized to generate variations in optical parameters.

Yet another mirror arrangement consists of utilizing a micromirror arrangement. One such micromirror structure consists of an array of mirrors, such as utilized in the Texas Instrument Digital Micromirror product.

Figure 10:
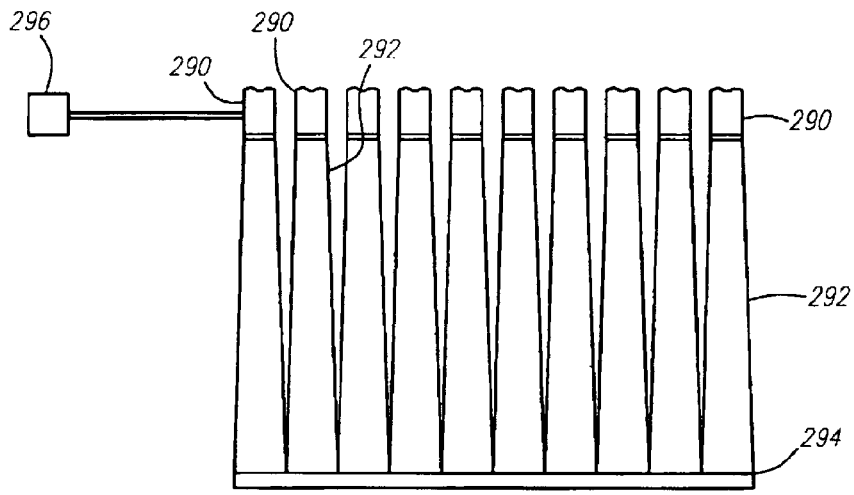
FIG. 10 is a side view of an array of illumination sources, illuminating a substrate or support.

FIG. 10 shows an alternate system for illumination in which multiple sources 290 are directed toward the sample plate or surface 294. Each source 290 is controlled by control system 296, with the various outputs 292 from the sources 290 illuminating the surface of the support 294.

Arrays of sources 290 may be fabricated in many ways. One preferable structure is a vertical cavity surface emitting laser (VCSEL) array. VCSEL arrays are known to those skilled in the art and serve to generate optical patterns with control of the various lasers comprising the VCSELs. Similarly, laser diode bars provide an array of sources. Alternatively, separate light sources may be coupled, such as through fiber optic coupling, to a region directed toward the surface 294.

The imaging system may serve function beyond the mirror imaging of the system. In addition to monitoring the intensity, size and shape of the optical fringes, it may be used for purposes such as calibration.

Optical Forces

The apparatus and methods of the instant inventions utilize, at least in part, forces on particles caused by light. In certain embodiments, a light pattern is moved relative to another physical structure, the particle or object, the medium containing the particle or object and/or the structure supporting the particle or object and the medium. Often times, a moving optical pattern, such as moving optical gradient field moves relative to the particles. By moving the light relative to particles, typically through a medium having some degree of viscosity, particles are separated or otherwise characterized based at least in part upon the optical force asserted against the particle. While most of the description describes the light moving relative to other structures, it will be appreciated that the relative motion may be achieved otherwise, such as by holding the light pattern stationary and moving the subject particle, medium and/or support structure relative to the optical pattern.

Figure 11A:
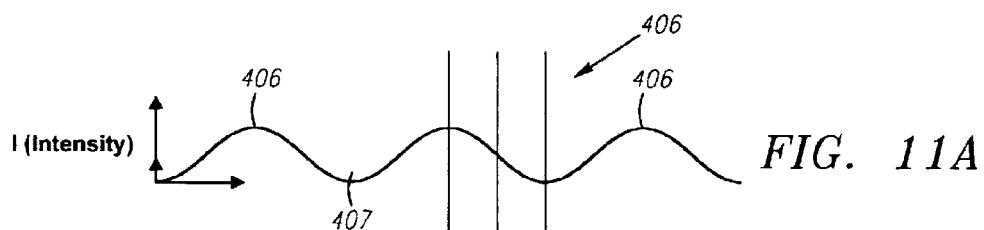
FIGS. 11A, 11B and 11C show graphs of intensity, forces and potential energy, respectively, as a function of position in one exemplary embodiment of the invention.
Figure 11B:
Figure 11C:
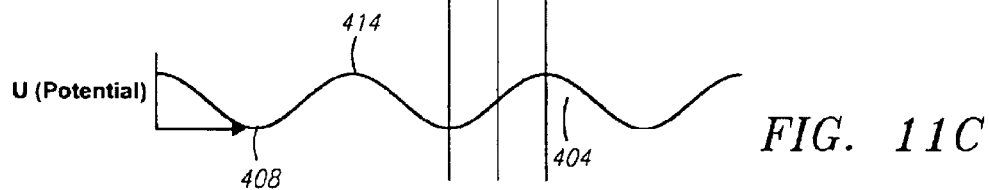

FIGS. 11A, 11B and 11C depict, respectively, the optical intensity profile, the corresponding optical force on a particle or cell and the corresponding potential energy of the particle in the optical intensity profile as a function of distance (x). FIG. 11A shows the intensity profile generated and applied against one or more particles. As shown, the intensity varies in a undulating or oscillating manner. The intensity, as shown, shows a uniform periodicity and symmetric waves. However, the intensity variations may be symmetric or asymmetric, or of any desired shape. The period may be fixed or may be variable. FIG. 11B shows the absolute value of the force as a function of position. The force is the spatial derivative of the intensity. FIG. 11C shows the potential energy as a function of position. The potential energy is the integrated force through a distance.

The profiles of FIGS. 11A–11C are shown to be generally sinusoidal. Generally, such a pattern would result from interference fringes. Differing profiles (of intensity, force and potential energy) may be desired. For example, it may be desirable to have a system where the potential energy well is relatively flat at the bottom and has steeper sides, or is asymmetric in its form.

Figure 12A:
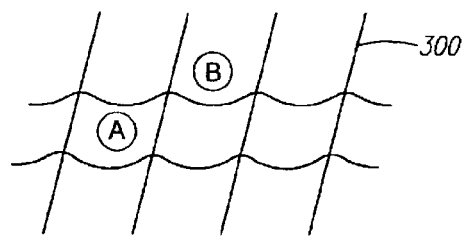
FIG. 12A shows two particles at first positions and a superimposed optical pattern.
Figures 12B, 12C:
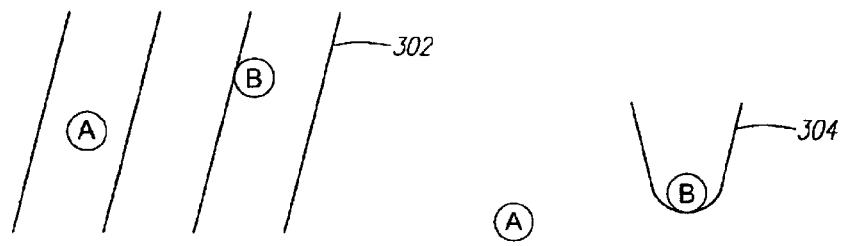
FIG. 12B shows the particles at second positions after illumination by the optical pattern.
FIG. 12C shows the trapping of particle B in an optical trap.

FIGS. 12A and 12B show two particles, labeled "A" and "B". in FIG. 12A, the particles are shown being illuminated by a two-dimensional intensity pattern 300. FIG. 12B shows the position of particles A and B at a later moment of time, after the intensity pattern has moved to position 302. In this example, the optical force has caused particle B to move relative to its prior position. Since the effect of the optical pattern 300 on particle A was less than on particle B, the relative positions of particles A and B are different in FIG. 12B as compared to FIG. 12A.

In one implementation of the system, the position of particles A and B in FIG. 12A would be determined. The system would then be illuminated with the desired gradient field, preferably a moving optical gradient field, and the system then imaged at a later point in time, such as shown in FIG. 12B. The absence of motion, or the presence of motion (amount of motion, direction of motion, speed of motion, etc.) may be utilized to characterize, or analyze the particle or particles. In certain applications, it may be sufficient to determine the response of a single particle to a particular optical pattern. Thus, information may be derived about the particle merely from the fact that the particle moved, or moved in a particular way or by a particular amount. That information may be obtained irrespective of the presence or absence of other particles. In yet other applications, it is desirable to separate two or more particles. In that case, by comparing the position of the particles relative to each other such as in FIG. 12A versus 12B, information regarding the particle may be obtained. Having determined which particle is the desired particle, assume for purposes of discussion to be particle B, the particle may then be separated from the other particles. As shown in FIG. 12C, an optical tweezer intensity profile 304 may be used to capture and remove particle B. Alternatively, as will be discussed in connection with FIGS. 14–19, the selected particle may be removed by other means, such as by fluidic means.

By utilizing a property of the particle, such as the optical dielectric constant, the light forces serve to identify, select, characterize and/or sort particles having differences in those attributes. Exposure of one or more particles to the optical force may provide information regarding the status of that particle. No separation of that particle from any other particle or structure may be required. In yet other applications, the application of the optical force causes a separation of particles based upon characteristics, such that the separation between the particles may result in yet further separation. The modes of further separation may be of any various forms, such as fluidic separation, mechanical separation, such as through the use of mechanical devices or other capture structures, or optically, such as through the use of an optical tweezer as shown in FIG. 12C, by application of a moving optical gradient, or by any other mode of removing or separating the particle, e.g., electromagnetic, fluidic or mechanical.

Figure 13A:
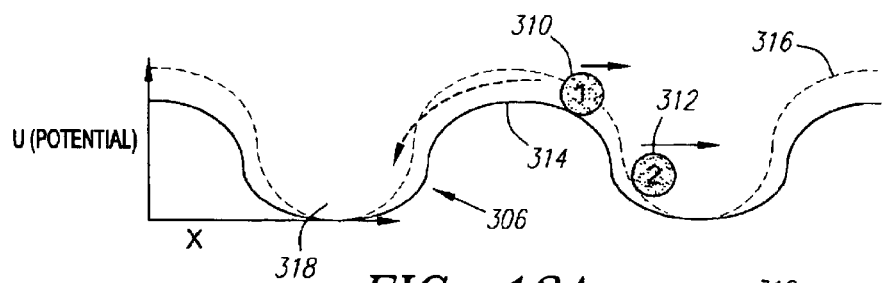
FIGS. 13A, 13B and 13C show graphs of the potential energy as a function of distance for the technique for separating particles.
Figures 13B, 13C:
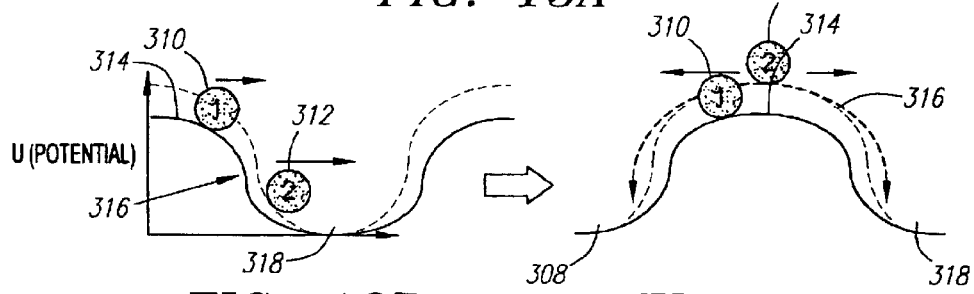

FIGS. 13A, 13B and 13C show potential energy as a function of distance for one exemplary mode of operation. The figures show particle 1 and particle 2 displaced in the x dimension relative to one another. The physical positioning of the two particles would typically be in the same plane, e.g., the same vertical plane. The figures show the potential energy of the particle. In FIG. 13A, particle 1 310 is subject to light intensity pattern creating the potential energy profile 314. Particle 2 312 is subject to the same light intensity pattern but is subject to the second potential energy profile 316. The second potential energy profile 316 is different from the first potential energy profile 314 because the dielectric constants are different between particle 1 310 and particle 2 312. In FIG. 5A, the light intensity pattern is moving toward the right. As the potential energy profiles 314, 316 move to the right, the particles 310, 312 experience different forces. Particle 1 310 will experience a smaller force as compared to particle 2 312, as depicted by the size of the arrows adjacent the particles. The force experienced by the particles is proportional to the spatial derivative of the potential energy. Thus, particle 2 312 being on a relatively "steeper" portion of the potential energy "wave" would be subject to a larger force. In FIG. 5A, the translation speed of the potential energy waves may be set to be larger than the speed at which particle 1 310 may move forward through the medium in which it is located. In that event, particle 1 310 may be subject to a force toward the left, FIG. 13A showing an arrow depicting the possible backward or retrograde motion of particle 1 310. The potential energy wells have a minimum 318 into which the particles would settle, absent motion or translation of the potential energy patterns 314, 316.

FIG. 13B shows particle 1 310 and particle 2 312 subject to the first potential energy 314 and second potential energy 316, respectively. As the potential energy patterns 314, 316 translate to the right, the particles 310, 312 are subject to a force to the right, though in different amounts as depicted by the relative size of the arrows. FIG. 13C shows the potential energy profiles 314, 316 after the potential energy profiles of FIG. 13B have been moved so as to place the potential energy maximum between particle 1 310 and particle 2 312. By "jerking" the intensity profiles 314, 316 forward quickly, particle 1 310 is then located on the "backside" of the potential energy "wave", and would be subject to a force to the left. The path of motion is then shown by the dashed arrow from particle 1 310. In contrast, particle 2 312 remains on the "front side" of the potential energy wave 316 and is subject to a force to the right. The effect of this arrangement is to cause further physical separation between particle 1 310 and particle 2 314. The potential energy profiles 314, 316 must be moved forward quickly enough such that the potential energy maximum is located between the particles to be separated, as well as to insure that the particle on the "backside" of the potential energy wave is caused to move away from the particle on the "front side" of the wave.

The apparatus and methods of these inventions utilize optical forces, either alone or in combination with additional forces, to characterize, identify, select and/or sort material based upon different properties or attributes of the particles. The optical profiles may be static, though vary with position, or dynamic. When dynamic, both the gradient fields as well as the scattering forces may be made to move relative to the particle, medium containing the particle, the support structure containing the particle and the medium. When using a moving optical gradient field, the motion may be at a constant velocity (speed and direction), or may vary in a linear or non-linear manner.

The optical forces may be used in conjunction with other forces. Generally, the optical forces do not interfere or conflict with the other forces. The additional forces may be magnetic forces, such as static magnetic forces as generated by a permanent magnet, or dynamic magnetic forces. Additional electric forces may be static, such as electrostatic forces, or may be dynamic, such as when subject to alternating electric fields. The various frequency ranges of alternating electromagnetic fields are generally termed as follows: DC is frequencies much less than 1 Hz, audio frequencies are from 1 Hz to 50 kHz, radio frequencies are from 50 kHz to 2 GHz, microwave frequencies are from 1 GHz to 200 GHz, infrared (IR) is from 20 GHz to 400 THz, visible is from 400 THz to 800 THz, ultraviolet (UV) is from 800 THz to 50 PHz, x-ray is from 5 PHz to 20 EHz and gamma rays are from 5 EHz and higher (see, e.g., Physics Vade Mecum).) The frequency ranges overlap, and the boundaries are sometimes defined slightly differently, but the ranges are always substantially the same. Dielectrophoretic forces are generated by alternating fields generally being in the single Hz to 10 MHz range. For the sake of completeness, we note that dielectrophoretic forces are more electrostatic in nature, whereas optophoretic forces are electromagnetic in nature (that is, comparing the frequency ranges is not meant to imply that they differ only in their frequency.) Gravitational forces may be used in conjunction with optical forces. By configuring the orientation of the apparatus, the forces of gravity may be used to affect the actions of the particle. For example, a channel may be disposed in a vertical direction so as to provide a downward force on a particle, such as where an optical force in the upward direction has been generated. The force of gravity takes into consideration the buoyancy of the particle. When a channel is disposed in the horizontal direction, other forces, e.g., frictional forces, may be present. Fluidic forces (or Fluidics) may be advantageously utilized with optical forces. By utilizing an optical force to effect initial particle separation, a fluidic force may be utilized as the mechanism for further separating the particles. As yet another additional force, other optical forces may be applied against the particle. Any or all of the aforementioned additional forces may be used singly or in combination. Additionally, the forces may be utilized serially or may be applied simultaneously.

FIGS. 14A and 14B show sorting of particles or objects from a one-dimensional source. As shown in FIG. 14A, particles 320 progress in a generally downward direction from a source in the direction of the arrow labeled particle flow. At junction 322, and possibly additionally before the junction 322, the particles are subject to an optical separation force. Those particles having a different response property, such as a different dielectric constant, may be separated from the line of particles resulting in the separated particles 326. Those particles which are not separated continue on as the particles 324. FIG. 14B shows optical cell sorting from a one-dimensional source. Cells 330 move in a fluid flow in a direction from top to bottom as shown by the arrow. The cells 330 are subject to an optical force in the region of junction 332. Selected cells 336 are deviated from the path of the original fluid flow. The remaining particles 334 continue on in the same direction as the original fluid flow. It will be appreciated that the term "selected" or "non-selected" or similar terminology as used herein is meant to be illustrative, and not intended to be limiting.

The techniques of this invention may be utilized in a non-guided, i.e., homogeneous, environment, or in a guided environment. A guided environment may optionally include structures such as channels, including microchannels, reservoirs, switches, disposal regions or other vesicles. The surfaces of the systems may be uniform, or may be heterogeneous.

FIG. 15 shows a plan view of a guided structure including channels. An input channel 340 receives particles 342 contained within a medium. An optical force is applied in region 344. The optical force would preferably be a moving optical gradient field. As the particles 342 move through the field 344, certain particles would be subject to a force causing them to move to the right in the channel as shown as particles 346, yet other particles 348 would move to the left of the T channel. By selection of the speed, orientation, periodicity, intensity and other parameters of the optical force gradient, the particles may be effectively separated.

The channels may be formed in a substrate or built upon some support or substrate. Generally, the depth of the channel would be on the order of from substantially 1 to substantially 2 diameters of the particle. For many biological cell sorting or characterization applications, the depth would be on the order of 10 to 20 $\mu$m. The width of the channels generally would be on the order of from substantially 2 to substantially 8 diameters of the particle, to allow for at least one optical gradient maximum with a width of the order of the particle diameter up to four or more optical gradient maxima with a width of the order of the particle diameter. For many biological cell sorting or characterization applications, the width would be of the order of 20 to 160 micrometers. The channels may have varying shapes, such as a rectangular channel structure with vertical walls, a V-shaped structure with intersecting non-planar walls, a curved structure, such as a semicircular or elliptical shaped channel. The channels, or the substrate or base when the channel was formed within it, may be made of various materials. For example, polymers, such as silicon elastomers (e.g., PDMS), gels (e.g., Agarose gels) and plastics (e.g., TMMA) may be utilized: glass, and silica are other materials. For certain applications, it may be desirable to have the support material be optically transparent. The surfaces may be charged or uncharged. The surface should have properties which are compatible with the materials to be placed in contact therewith. For example, surfaces having biological compatibility should be used for biological arrays or other operations.

Various forms of motive force may be used to cause the particles, typically included within a fluid, to move within the system. Electroosmotic forces may be utilized. As known in the art, various coatings of the walls or channels may be utilized to enhance or suppress the electroosmotic effect. Electrophoresis may be used to transport materials through the system. Pumping systems may be utilized such as where a pressure differential is impressed across the inlet and outlet of the system. Capillary action may be utilized to cause materials to move through the system. Gravity feeding may be utilized. Finally, mechanical systems such as rotors, micropumps, centrifugation may be utilized.

FIG. 16 shows an "H" channel structure for sorting of particles. The H-shaped structure has two inlets and two outlets. The inlet 350 receives both fluid and the subject particles 352 to be sorted. Fluid is input in the second input arm of the H channel. The main or connecting channel 356 receives the fluid flow from both inputs. In the connecting channel 356, the particles 354 will flow through the connecting channel and be subject to the optical sorting force 358. At that stage, the particles are then separated based upon the differentiating parameter, such as the particle's dielectric constant. The particles being moved from the primary stream move as particles 360 to one output. The particles 362 which are not diverted by action of the optical force 358 continue to the left hand outlet 364. Laminar flow within the system will cause the particles 354 to move through the main channel 356, and if the channel width is large enough, will tend to cause the particles 354 to flow relatively closer to the wall nearer the input. The sorting process then consists of diverting the particle from the laminar flow adjacent the left wall to the laminar flow which will divert to the right hand output.

FIG. 17 shows a wide channel structure for particle separation. Input 370 receives the particles 372 in a fluidic medium. The particles are subject to an optical sorting force 374, whereupon the diverted particles 378 flow toward outlet 382 and particles 376 flow toward outlet 380.

FIG. 18 shows an X-channel structure for sorting. Input 390 receives particles 392 in a fluidic medium. Second input 394 received fluid. The particles 392 are then subject to an optical sorting force 396. Diverted particles 402 flow to exit 404. Particles 398 flow to exit 400.

Figure 19:
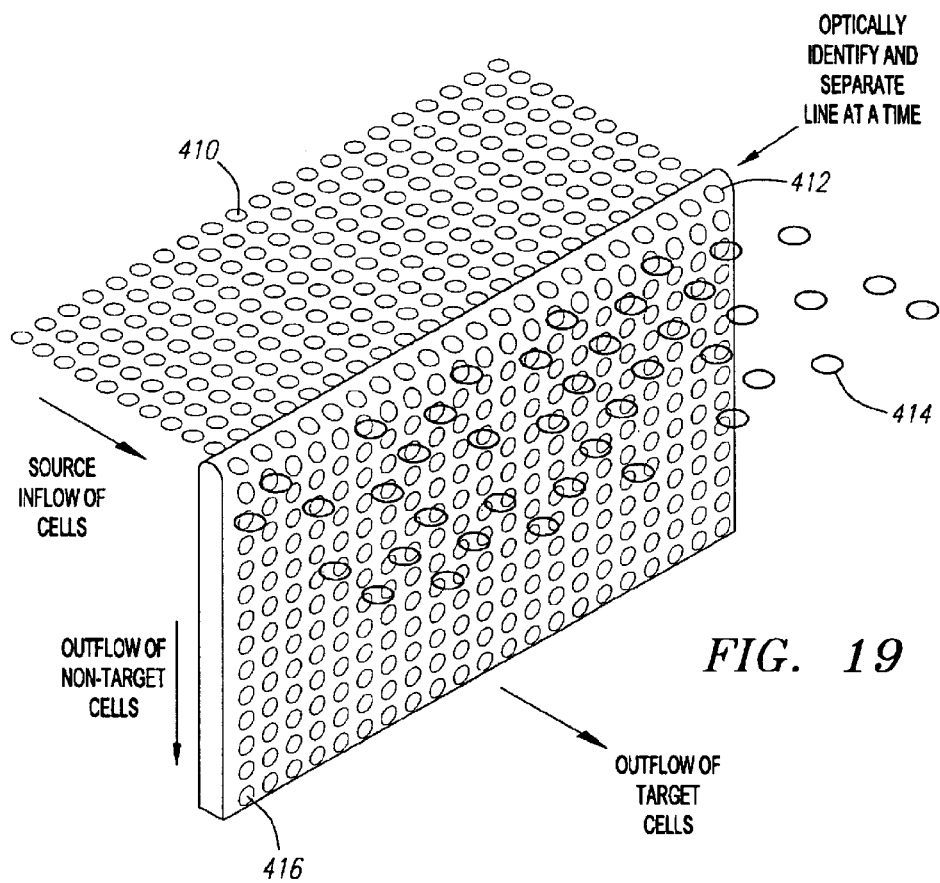
FIG. 19 is a perspective view of a two-dimensional sorting structure.

FIG. 19 is a perspective drawing of a two-dimensional sorting system. The source inflow of cells 410 intersect with an optical sorting force along line 412. The sorting force 412 results in an outflow of target cells 414 in one-dimension, typically in one plane, and an outflow of non-target cells 416 in another plane. The plane of outflow of targets cells 414 is non-coplanar with the plane of outflow of non-target cells 416.

Figure 20:
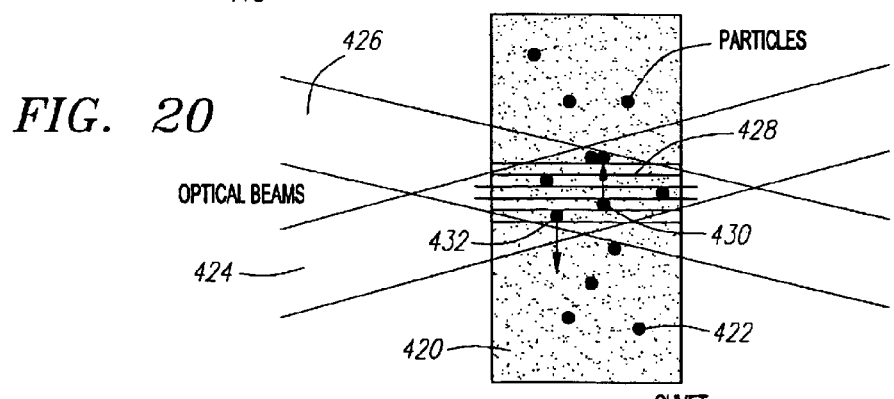
FIG. 20 is a plan view of a multi-dimensional sorting structure.

FIG. 20 shows an arrangement comprising a three-dimensional cell sorting arrangement. A volume 420, most preferably a substantially three-dimensional volume, though possibly a volume of lower effective dimensionality, contains particles 422. An optical force gradient 428 is generated within the volume 420 to effect particle sorting. One embodiment for generating the optical field gradient 428 is to interfere first beam 424 with a second beam 426. The first beam 424 and second beam 426 interfere and generate the force pattern 428. As shown, a first particle 430 is subject to a force in a direction from bottom to top, whereas a second particle 432 is subject to a force from top to bottom. Alternately, the optical pattern 428 may cause forces on particles 430, 432 in the same direction, but with differing amounts of force.

Figure 21:
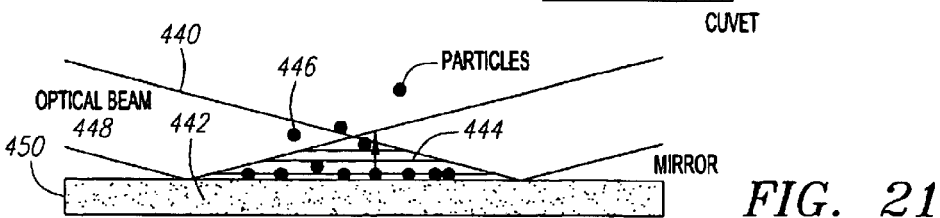
FIG. 21 is a side view of a multi-dimensional sorting structure including a reflective surface for generation of the optical gradient pattern.

FIG. 21 shows an embodiment having multiple degrees of freedom, preferably three degrees of freedom. The volume 440 contains particles 442 which are disposed adjacent a surface, near the inwardly disposed surface of mirror 450. An optical gradient force 444 is generated which causes selected ones of the particles 446 at the surface to be moved into the volume 440 such as particle 446. The optical force gradient 444 may be generated by shining an optical beam 448 onto a mirror 450, which causes interference between the beam 448 and its reflected beam.

Figure 22:
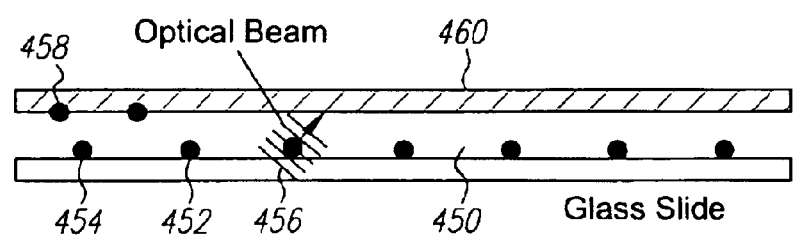
FIG. 22 is a side view of a sorting structure including a capture structure.

FIG. 22 shows a multi-dimensional system in which a volume 450 is utilized to separate particles. First particles 452 are disposed adjacent the surface of the slide 454. A light intensity pattern 456 causes displacement of selected particles. Those displaced particles may then be attached to a sticky or adhesive mat 460 and comprises particles 458.

Figure 23:
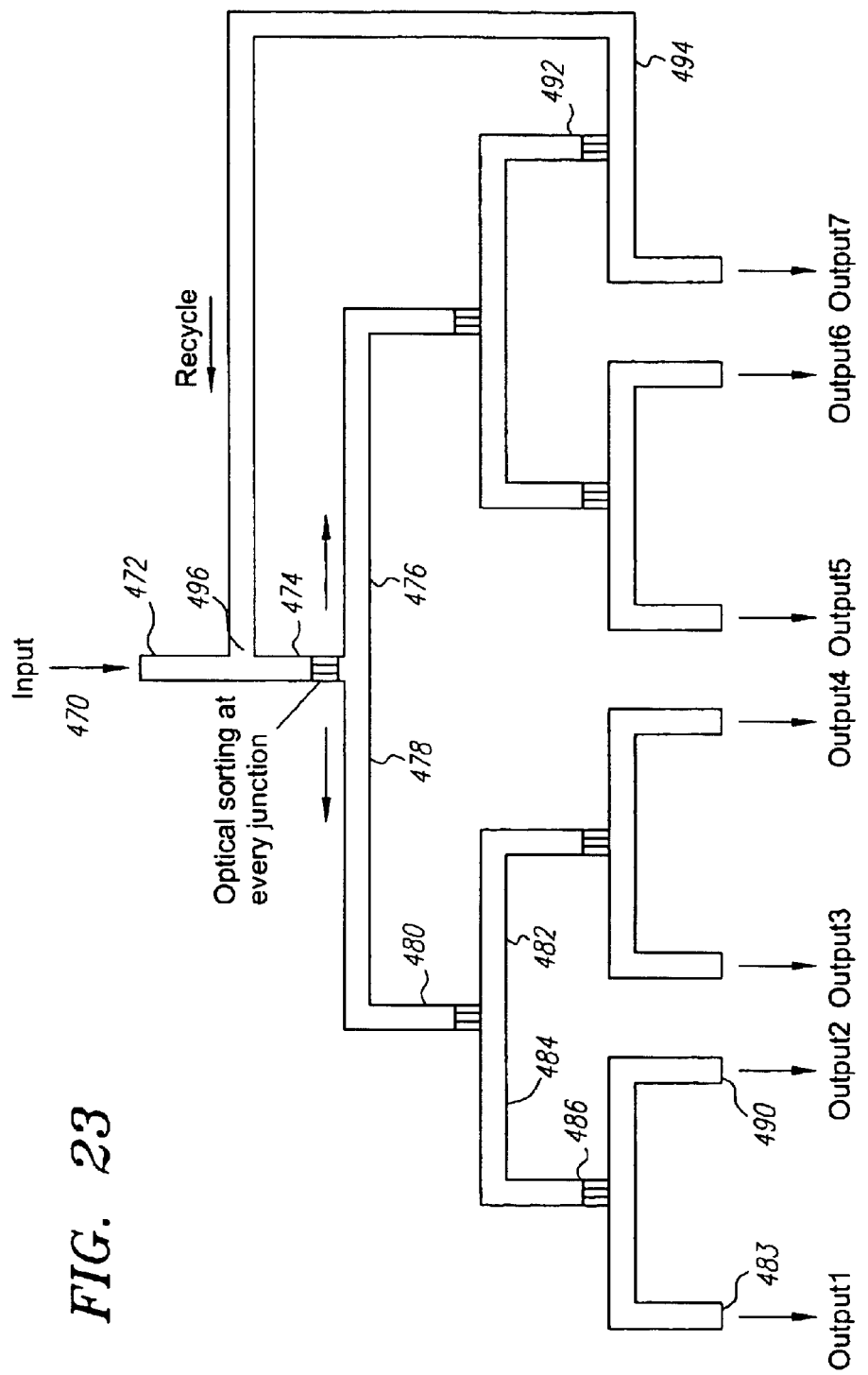
FIG. 23 is a plan view of a microfluidic system including a recycle path.

FIG. 23 shows a plan view of a complex channel based system for sorting, characterization or classification. An input 470 leads through channel 472 to a first optical sorting region 474. The sorting at a given channel is as described, before. The output of the sorting results in a first set of particles 478 and a second set of particles 476. The first set of particles 478 flows to the second optical sorting region 480. As before, the particles are sorted into first particles 484 and second particles 482. A next optical sorting region 486 results in the output of sorted particles, the first output 488 and second output 490 then leading to further collection, counting or analysis. In one aspect, the complex system may include one or more recycle or feedback tabs 490. As shown, the output from the optical force region 492 includes output 7 but also a recycle path 494 leading to the input 496 coupling to the channel 472. Such a recycle system might be used in an enrichment system.

The systems described herein, and especially a more complex system, may include various additional structures and functionalities. For example, sensors, such as cell sensors, may be located adjacent various channels, e.g., channel 742. Various types of sensors are known to those skilled in the art, including capacitive sensors, optical sensors and electrical sensors. Complex systems may further include various holding vessels or vesicles, being used for source materials or collection materials, or as an intermediate holding reservoir. Complex systems may further include amplification systems. For example, a PCR amplification system may be utilized within the system. Other linear or exponential biological amplification methods known to those skilled in the art may be integrated. Complex systems may further include assays or other detection schemes. Counters may be integrated within the system. For example, a counter may be disposed adjacent an output to tally the number of particles or cells flowing through the output. The systems of the instant invention are useable with microelectromechanical (MEMs) technology. MEMs systems provide for microsized electrical and mechanical devices, such as for actuation of switches, pumps or other electrical or mechanical devices. The system may optionally include various containment structures, such as flow cells or cover slips over microchannels.

A computerized workstation may include a miniaturized sample station with active fluidics, an optical platform containing a laser (e.g., a near infrared laser for biological applications) and necessary system hardware for data analysis and interpretation. The system may include real-time analysis and testing under full computer control.

The inventions herein may be used alone, or with other methods of cell separation. Current methods for cell separation and analysis include flow cytometry, density gradients, antibody panning, magnetic activated cell sorting ("MACS™"), microscopy, dielectrophoresis and various physiological and biochemical assays. MACS separations work only with small cell populations and do not achieve the purity of flow cytometry. Flow cytometry, otherwise known as Fluorescent Activated Cell Sorting ("FACS™") requires labeling.

In yet another aspect, the systems of the present invention may optionally include sample preparation steps and structure for performing them. For example, sample preparation may include a preliminary step of obtaining uniform size, e.g., radius, particles for subsequent optical sorting.

The systems may optionally include disposable components. For example, the channel structures described may be formed in separable, disposable plates. The disposable component would be adapted for use in a larger system that would typically include control electronics, optical components and the control system. The fluidic system may be included in part in the disposable component, as well as in the non-disposable system components.

FIG. 24 shows a system for optical sorting based upon a physical parameter of the object, such as deformability. An optical gradient 500 may illuminate particles 502, 504. Particle 504 is more deformable than particle 502. As a result, given the periodicity of the optical force pattern 500, the deformable particle 504 may be subject to a relatively larger force, and move more under the optical field 500. Preferably, the optical field 500 is a moving optical gradient field. Alternatively, the particles 502, 504 may be subject to the optical force 500, and the structure of the particles 502, 504 monitored. In that way, by observing the deformability of the particles, relative to the light pattern 500, the particles may be identified, classified or otherwise sorted.

FIG. 25 shows a method for sorting particles based upon size. An optical intensity pattern 510 illuminates larger particle 512 and smaller particle 514. The differently sized particles 512, 514 are subject to different forces. Where, for example, larger particle 512 spans two or more intensity peaks of the optical gradient 510, the particle may have no net force applied to it. In contrast, the smaller particle 514 which has a size smaller than the period of the optical intensity pattern 510 may be subject to a relatively larger force. By selection of the period of the optical pattern 510 relative to the size of particles to be sorted, the system may effectively sort based upon size. In one method, a set of particles may be subject to an increasing period of the light intensity, such that smaller particles are removed first, followed by the relatively larger particles at a later time. In this way, particles may be effectively sorted by size.

Methods for Reducing or Modifying Forces

The system and methods may include various techniques for reducing or otherwise modifying forces. Certain forces may be desirable in certain applications, but undesirable in other applications. By selecting the technique to reduce or minimize the undesired forces, the desired forces may more efficiently, sensitively and specifically sort or identify the desired particles or conditions. Brownian motion of particles may be an undesired condition for certain applications. Cooling of the system may result in a reduced amount of Brownian motion. The system itself may be cooled, or the fluidic medium may be cooled.

Figure 4A:
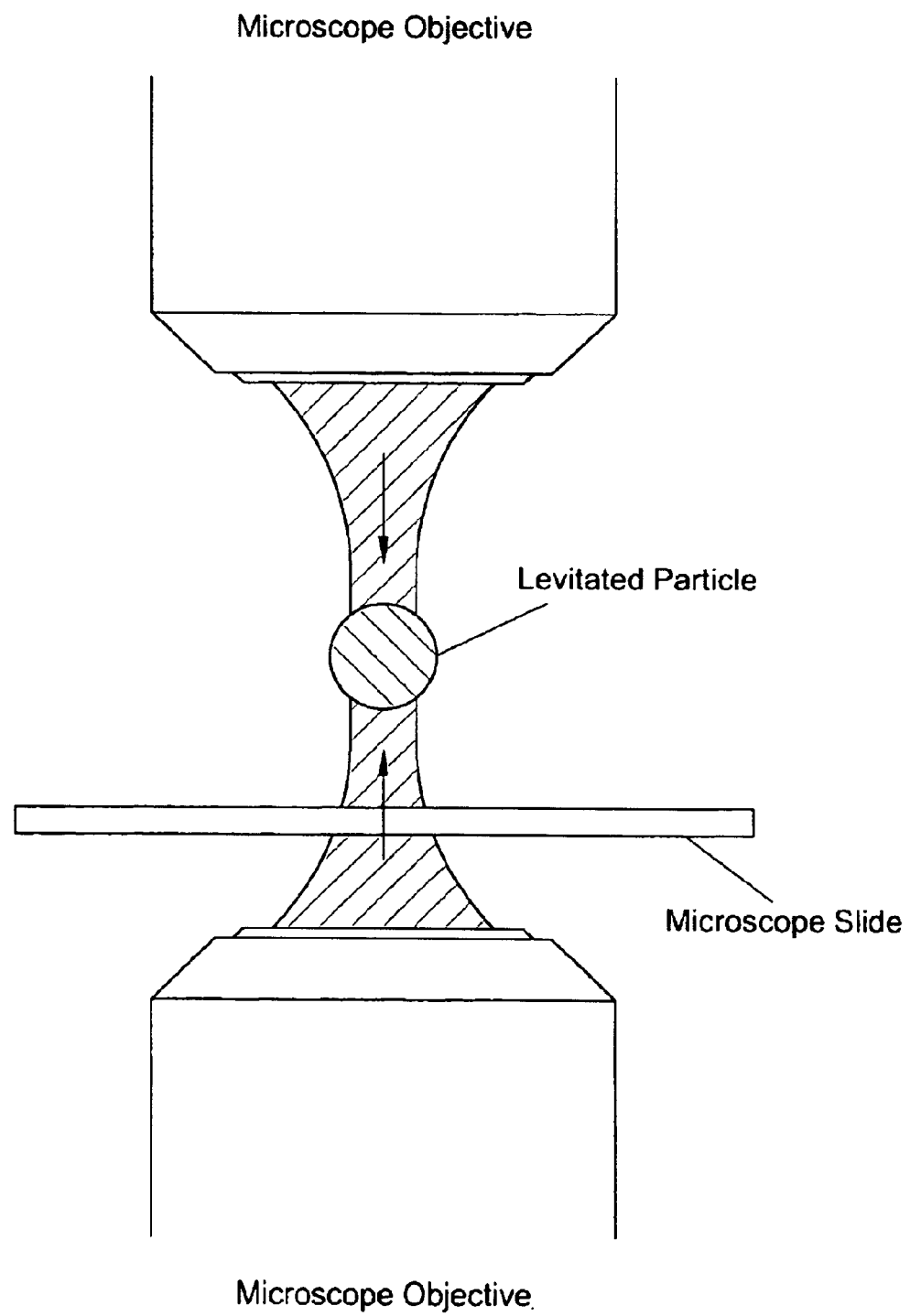
FIG. 4A is a side view of an alternate optical arrangement utilizing counterpropagating beams for particle levitation.

Yet another force which may be undesired in certain applications is friction or other form of sticking force. If surface effects are to be minimized, various techniques may be utilized. For example, a counterpropagating beam arrangement may be utilized to capture particles and to remove them from contact with undesired surfaces. Alternatively, the particles may be levitated, such as through the use of reflected light (see, e.g., FIG. 4, mirror 108). FIG. 4A shows an alternative arrangement for particle levitation. Opposing forces of two counter-propagating optical beams can be used to levitate a particle to reduce surface friction drag.

Yet other techniques exist for addressing friction, stiction, electrostatic and other surface interactions which may interfere with the mobility of cells and/or particles. For example, surfaces may be treated, such as through the use of covalent or non-covalent chemistries, which may moderate the frictional and/or adhesion forces. Surfaces may be pretreated to provide better starting surfaces. Such pretreatments may include plasma etching and cleaning, solvent washes and pH washes, either singly or in combination. Surfaces may also be functionalized with agents which inhibit or minimize frictional and adhesive forces. Single or multi-step, multilayer chemistries may be utilized. By way of example, a fluorosilane may be used in a single layer arrangement which renders the surface hydrophobic. A two-step, two-layer chemistry may be, for example, aminopropylsilane followed by carboxy-PEG. Teflon formal coating reagents such as CYTOP™ or Parylene™ can also be used. Certain coatings may have the additional benefit of reducing surface irregularities. Functional groups may, in certain cases, be introduced into the substrate itself. For example, a polymeric substrate may include functional monomers. Further, surfaces may be derivitized to provide a surface which is responsive to other triggers. For example, a derivatized surface may be responsive to external forces, such as an electric field. Alternatively, surfaces may be derivatized such that they selectively bind via affinity or other interactions.

Yet another technique for reducing surface interactions is to utilize a biphasic medium where the cells or particles are kept at the interface. Such aqueous polymer solutions, such as PEG-dextran partition into two phases. If the cells partitioned preferentially into one of the layers, then under an optical gradient the cells would be effectively floating at the interface.

Methods for Enhancing or Changing the Dielectric Constant

Optionally, the particles to be subject to the apparatus and methods of these inventions may be either labeled or unlabeled. If labeled, the label would typically be one which changes or contributes to the dielectric constant of the particle or new particle (i.e., the initial particle and the label will act as one new particle). For example, a gold label or a diamond label would effectively change most typical dielectric constants of particles.

Yet other systems may include an expressible change in dielectric constant. For example, a genetic sequence may exist, or be modified to contain, an expressible protein or other material which when expressed changes the dielectric constant of the cell or system. Another way to tune the dielectric constant of the medium is to have a single medium in a fluidic chamber where the dielectric constant can be changed by changing the temperature, applying an electric field, applying an optical field, etc. Other examples would be to dope the medium with a highly birefringent molecule such as a water-soluble liquid crystal, nanoparticles, quantum dots, etc. In the case of birefringent molecules, the index of refraction that the optical beam will see can be altered by changing the amplitude and direction of an electric field.

Methods for Increasing Sensitivity

Maximizing the force on a particle for a given intensity gradient suggests that the difference in dielectric constant between the particle and medium should be maximized. However, when sensitivity is required in an application, the medium should be selected such that the dielectric constant of the medium is close to the dielectric constant of the particle or particles to be sorted. By way of example, if the particle population to be sorted has dielectric constants ranging from 1.25 to 1.3, it would be desirable to choose a dielectric constant which is close to (or even within) that range. For cells, a typical range of dielectric constants would be from 1.8 to 2.1. By close, a dielectric constant within 10% or, more particularly, within 5%, would be advantageous. While the absolute value of the magnitude of the force on the particle population may be less than in the case where the dielectric constant differs markedly from the dielectric constant of the medium, the difference in resulting motion of the particles may be larger when the dielectric constant of the medium is close to the range of dielectric constants of the particles in the population. While utilizing the increased sensitivity of this technique at the outset, once the separation begins, the force may be increased by changing the dielectric constant of the medium to a more substantial difference from the dielectric constants of the particle or particle collection. As indicated, it is possible to choose the dielectric constant of the medium to be within the range of dielectric constants of the particle population. In that instance, particles having a dielectric constant above the dielectric constant of the medium will feel a force in one direction, whereas those particles having a dielectric constant less than the dielectric constant of the medium will feel a force moving in the opposite direction.

Scattering Force Systems

It is possible to utilize the scattering force, either alone or in combination with the optical gradient force, such as supplied by a moving optical field gradient, for separation of particles. FIG. 26 shows the before and after depiction of a system including a laser 520 and a lens 522 which collimates the optical beam. A capillary 524 receives the illumination, preferably along its axis. A set of particles, first particles 526 and second particles 528, are illuminated by the light beam and are subject to different scattering forces depending upon their different scattering properties. Because of the different forces, first particles 526' move a shorter distance than second particles 528', as shown in the second drawing. In this way, optical forces, particularly optical scattering forces, may be utilized to separate particles.

FIGS. 27A, 27B and 27C depict a scattering force switch. A first input 530 couples via a channel to a first output 536. The second input 532 couples to a second output 538 via a channel. The two channels overlap by providing a fluidic connection between them. In operation, a particle entering in input 1 530 may be switched by a scattering force switch 540 by deviating the particle from the channel coupled to input 1 530 to the channel containing output 2 538. Scattering force switches may be used in conjunction with the optical gradient force systems, especially the moving optical gradient force systems described herein.

Static Systems

FIG. 28 shows a system for the measurement of dielectric constants of particles. A particle 558 having a dielectric constant may be subject to different media having different dielectric constants. As shown, a first vessel 550, a second vessel 552, and so on through an end vessel 554 contain a medium having different dielectric constants $\in_1 \in_2, \ldots \in_n$, respectively. By illuminating the particle 558 with an optical gradient force 556, and observing the motion, the dielectric constant of the particle may be determined. If the dielectric constant of the medium is equal to the dielectric constant of the particle then no force is imposed by the optical illumination 556. In contrast, if there is a difference between the dielectric constant of the particle and the dielectric constant of the medium, an optical force will be imposed on the particle by the optical illumination 556. Different dielectric constant media may be supplied as shown in FIG. 28, namely, where a plurality a vessels 550, 552 . . . 554 are provided. Alternately, a particle may be subject to a varying dielectric constant over time, such as through use of a titration system. In on implementation, the titration may be accomplished in a tube containing the particle by varying the dielectric constant of the fluid over time, such as by mixing fluids having different dielectric constants, preferably at the inlet to the tube, or by providing a varying dielectric constant profile, such as a step profile. Additionally, the dielectric constant of a particle may be approximated by interpolation, such as where two or more data points are obtained regarding the force on the particle in different media, and then the expected dielectric constant in which no force is present may be determined.

FIG. 29 shows a static system in which separation may occur. A light pattern 560 illuminates first particle 562 and second particle 564. If the dielectric constant of the first particle 562 is less than the dielectric constant of the medium, then the particle moves toward an area of lower intensity. In contrast, if the second particle 564 has a dielectric constant which is greater than the dielectric constant of the medium, the particle will move toward the region of higher intensity. As a result, the first particle 562 and second particle 564 are subject to forces in opposite directions. Given the proximity shown, they would move away from one another.

Figure 30:
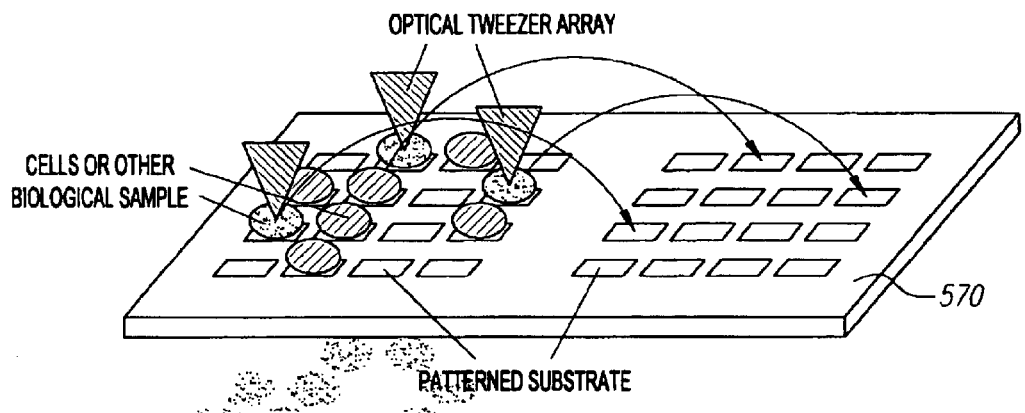
FIG. 30 is a perspective view of a optical tweezer array.

FIG. 30 shows a system for the use of a plurality of optical tweezers, preferably in an array, such as to move materials. A substrate 570 may contain one or more sites 572 on which materials may be placed. The materials may comprise particles, cells, or any other material to be selected or moved. An optical tweezer array may selectively move materials, such as those shown as light circles 576, and move those materials to yet another portion of the substrate 570, such as array 574. Alternatively, the optical tweezer array may illuminate the entire array 572, and then selectively move the materials as to which the optical tweezer array provides sufficient force to cause separation of the particles 576, 578 from the array 572 on the substrate 570. For example, the particles may have attachment mechanisms, such as complimentary nucleic acids, which selectively bind them to the substrate 570.

Figure 31:
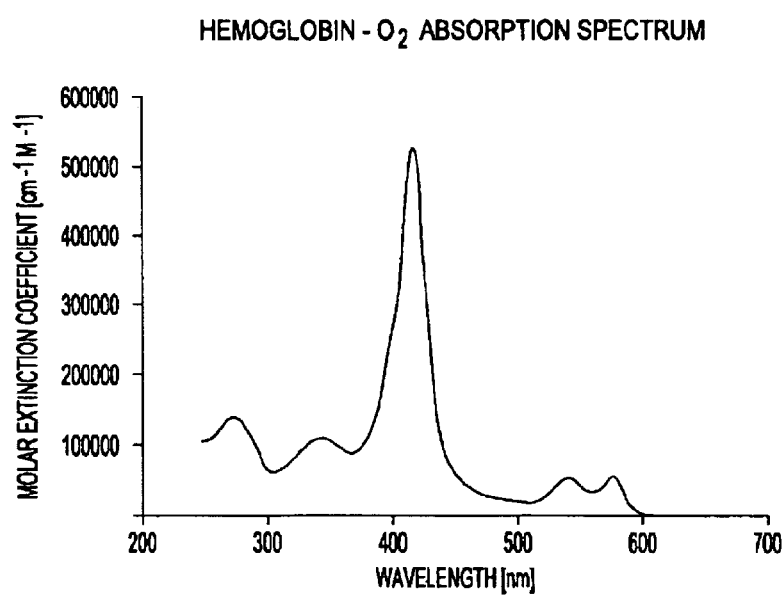
FIG. 31 is a graph of molar extinction coefficient as a function of wavelength for hemoglobin-$O_2$ absorption spectrum.

FIG. 31 shows a graph of molar extinction coefficient as a function of wavelength for hemoglobin-$O_2$ absorption. For certain sorting applications, it may be desirable to select a wavelength for illumination which is at or near a peak of absorption. For example, it may be desirable to choose a wavelength at the 500,000 molar extinction coefficient peak. Alternatively, it may be desirable to choose a secondary peak, e.g., the peak at substantially 560 nm or at substantially 585 nm.

The first setup is a moving fringe workstation for optophoresis experiments. A high power, 2.5 watt, Nd-YAG laser (A) is the near IR, 1064 nm wavelength, light source. The fringe pattern is produced by directing the collimated laser beam from the mirror (1) through the Michelson interferometer formed by the prism beam splitter (2) and the carefully aligned mirrors (3). A variable phase retarder (4) causes the fringe pattern to continuously move. This fringe pattern is directed by the periscope (5) through the telescope (5a) and (5b) to size the pattern to fill the back focal plane of the microscope objective, and then is directed by the dichroic beam splitter (6) through a 20× microscope objective (7) to produce an image of the moving fringe pattern in the fluidic chamber holding the sample to be sorted. A second, 60× microscope objective (8) images the flow cell onto a CCD camera to provide visualization of the sorting experiments. A fiber-optic illuminator (9) provides illumination, through the dichroic beam splitter (6), for the sample in the fluidic chamber. The fluidic chamber is positioned between the two microscope objectives by means of an XYZ-translation stage.

It will be appreciated by those skilled in the art that there are any number of additional or different components which may be included. For example, additional mirrors or other optical routing components may be used to 'steer' the beam where required. Various optical components for expanding or collimating the beam may be used, as needed. In the set-up implementing FIG. 5, the laser used additional mirrors to steer the laser beam into the spatial filter, which that produced a well collimated Gaussian beam that is then guided to the Michelson interferometer.

The second setup is a workstation for measuring and comparing the dielectric properties of cells and particles at near IR optical frequencies, using a 600 mW, ultra-low noise Nd-YAG laser (B) as a light source. The remainder of the optical setup is similar to the moving fringe workstation, except there is no interferometer to produce moving fringes. Instead a single, partially focused illumination spot is imaged within the fluidic chamber. The interaction of cells with this illumination field provides a measurement of the dielectric constant of the cells at near IR optical frequencies.

Exemplary Applications

High Throughput Biology

The methods and apparatus herein permit a robust cell analysis system suitable for use in high throughput biology in pharmaceutical and life sciences research. This system may be manufactured using higher performance, lower cost optical devices in the system. A fully integrated high throughput biology, cell analysis workstation is suitable for use in drug discovery, drug discovery, toxicology and life science research. These systems may utilize advanced optical technologies to revolutionize the drug discovery process and cellular characterization, separation and analysis by integrating optophoresis technology into devices for the rapid identification, selection and sorting of specific cells based on their innate properties, including their innate optical dielectric properties. In addition, since the technology is based on the recognition of such innate properties, labels are not required, greatly simplifying and accelerating the testing process. The lasers employed are preferably in the biologically-compatible infrared wavelengths, allowing precise cell characterization and manipulation with little or no effect on the cell itself. The technology is suited to the post-genomics era, where the interaction of the cell's molecular design/make-up (DNA, RNA and proteins) and the specific cellular changes (growth, differentiation, tissue formation and death) are of critical importance to the basic understanding of health and disease.

The Optophoresis technology changes the nature of cell-based assays. Applications would include all methods of cellular characterization and sorting. The technology also offers diverse applications in the areas of molecular and cellular physiology. Optophoresis technology addresses fundamental properties of the cell itself, including its optical dielectric properties. The optophoretic properties of the cell change from cell type to cell type, and in response to external stimuli. These properties are reflective of the overall physiologic status of the cell. Active cells have dielectric properties that are different from resting cells of the same type. Cancer cells have different optophoretic properties than their normal counterparts. These cellular properties can also be used effectively in drug discovery and pharmaceutical research, since nearly all drugs are targeted ultimately to have direct effects on cells themselves. In other words, drugs designed to effect specific molecular targets will ultimately manifest their effects on cellular properties as they change the net dielectric charge of the cell. Therefore, rapid screening of cells for drug activity or toxicity is an application of the technology, and may be referred to as High Throughput Biology. Other main applications include drug discovery and pharmaceutical research.

The Human Genome Project and other associated genome programs will provide enormous demand for improved drug development and screening technologies. Sophisticated cellular approaches will be needed for cost-effective and functional screening of new drug targets. Likewise, information from the genome projects will create demand for improved methods of tissue and organ engineering, each requiring access to well characterized cellular materials. Moreover, optical technology from the information and telecommunications industry will provide the system hardware for improved optical cell selection and sorting. The price/performance ratios for high powered near infrared and infrared lasers originally developed for telecommunications applications continue to improve significantly. In addition, solid-state diode lasers may be used having a variety of new wavelengths, with typically much higher power output than older versions. Vertical Cavity Surface Emitting Lasers ("VCSELs") provide arrays of diode lasers at very reasonable costs with increasing power output.

A computerized Workstation may be composed of a miniaturized sample station with active fluidics, an optical platform containing a near infrared laser and necessary system hardware for data analysis and interpretation. The system includes real-time analysis and testing under full computer control. Principal applications of the technology include cell characterization and selection, particularly for identifying and selecting distinct cells from complex backgrounds.

Importantly, unlabelled, physiologically normal, intact test cells will be employed in the system. The sample is quickly analyzed, with the cells classified and sorted by the optical field, thereby allowing characterization of drug response and identify toxicity or other measures of drug efficacy. Characterizing the cellular optophoretic properties uniquely associated with various drug testing outcomes and disease states is a part of this invention. Identification of these novel parameters constitutes useful information.

An integrated system may, in various aspects, permit: the identification, selection and separation of cells without the use of labels and without damaging the cells; perform complex cell analysis and separation tasks with ease and efficiency; observe cells in real time as they are being tested and manipulated; establish custom cell sorting protocols for later use; isolate rare cells from complex backgrounds; purify and enrich rare cells (e.g. stem cells, fragile cells, tumor cells); more easily link cell phenotype to genotype; study cell—cell interactions under precise and optical control; and control sample processing and analysis from start to finish.

The technology offers a unique and valuable approach to building cellular arrays that could miniaturize current assays, increase throughput and decrease unit costs. Single cell (or small groups of cells) based assays will allow miniaturization, and could allow more detailed study of cell function and their response to drugs and other stimuli. This would permit cellular arrays or cell chips to perform parallel high-throughput processing of single cell assays. It could also permit the standardization of cell chip fabrication, yielding a more efficient method for creation of cell chips applicable to a variety of different cells types.

Mammalian cell culture is one of the key areas in both research (e.g., discovery of new cell-produced compounds and creation of new cell lines capable of producing specific proteins) and development (e.g., developing monoclonal cell lines capable of producing highly specific proteins for further research and testing). Mammalian cell culture is also a key technology for the production of new biopharmaceuticals on a commercial scale.

Once researchers have identified drug targets, compounds or vaccines, mammalian cell culture is an important technology for the production of quantities necessary for further research and development. There are currently more than 70 approved biotechnology medicines and more than 350 such compounds in testing, targeting more than 200 diseases.

Optical cell characterization, sorting and analysis technologies could be useful in selecting and separating lines of mammalian cells according to whether they produce a new protein or biopharmaceutical compound and according to the yield of the protein or compound. Cell yield is a key factor in determining the size of the plant a manufacturer must build to produce commercial quantities of a new biotechnology drug.

We turn now to more specific discussions of applications. First, we address separation applications, and second, address monitoring applications.

Separation Applications

White cells from red cells. White blood cells are the constituents of blood which are responsible for the immune response as compared with red cells which transport oxygen through the body. White cells need to be removed from red cells prior to transfusion for better tolerance and to decrease infection risks. It is also often important to remove red cells in order to obtain enriched populations of white cells for analysis or manipulation. Optophoresis can allow the separation of these two distinct cell populations from one another for use in applications where a single population is required.

Reticulocytes from mature red blood cells. Reticulocytes, which are immature red blood cells normally found at very low levels can be indicators of disease states when they are found at increased levels. This application would use optophoresis for the separation and enumeration of the levels of reticulocytes from whole blood.

Clinical Care Applications, e.g., Fetal stem cells from maternal circulation. The Clinical Care applications include cell-based treatments and clinical diagnostics. The successful isolation of fetal cells from maternal blood represents a source of fetal DNA obtainable in a non-invasive manner. A number of investigators worldwide have now demonstrated that fetal cells are present in the maternal circulation and can be retrieved for genetic analysis. The major current challenges in fetal cell isolation include selection of the target fetal cell type, selection and isolation of the cells and the means of genetic analysis once the cells are isolated. Using a maternal blood sample, the system can identify the rare fetal cells circulating within the mother's blood and to permit the diagnosis of genetic disorders that account for up to 95% of prenatal genetic abnormalities, e.g., Down's Syndrome. Cell-based treatments refer to procedures similar to diagnostic procedures, but for which the clinical purpose is somewhat broader. During pregnancy, a small number of fetal cells enter the maternal circulation. By purifying these cells using optophoresis prenatal diagnosis of a variety of genetic abnormalities would be possible from a single maternal blood sample.

Clinical Care Applications, e.g., Stem Cell Isolation. The purpose of stem cell isolation is to purify stem cells from stem cell grafts for transplantation, i.e., to remove T-cells in allogeneic grafts (where the donor and the recipient are not the same person) and cancer cells in autologous grafts (where the donor and the recipient are the same person). Currently stem cell technologies suffer from several drawbacks. For example, the recovery efficiency of stem cells obtained using currently available systems is on the order of 65–70%. In addition, current methods do not offer the 100% purity which is beneficial in transplant procedures.

Tumor cells from blood. Minimal Residual Disease (MRD) Testing The National Cancer Institute (NCI) estimates that approximately 8.4 million Americans alive today have a history of cancer, and that over 1.2 million new cancer cases were diagnosed in 2000. The NCI also estimates that since 1990 approximately 13 million new cancer cases were diagnosed, excluding noninvasive and squamous cell skin cancers. Optophoresis technology addresses some of the key unmet needs for better cancer screening, including: accurate, reproducible and standardized techniques that can detect, quantify and characterize disseminated cancer cells; highly specific and sensitive immunocytological techniques; faster speed of cell sorting; and techniques that can characterize and isolate viable cancer cells for further analysis.

Cancer cells may be found in low numbers circulating in the blood of patients with various forms of that disease, particularly when metastasis has occurred. The presence of tumor cells in the blood can be used for a diagnosis of cancer, or to follow the success or failure of various treatment protocols. Such tumor cells are extremely rare, so a means of enrichment from blood such as optophoresis would need to be employed in order to have enough cells to detect for accurate diagnosis. Another application for optophoresis in this regard would be to remove tumor cells from blood or stem cell products prior to them being used to perform an autologous transplant for a cancer patient.

Fetal stem cells from cord blood. The umbilical cord from a newborn generally contains blood which is rich in stem cells. The cord blood material is usually discarded at birth; however, there are both academic and private concerns who are banking cord blood so that such discarded material can be used for either autologous or allogenic stem cell replacement. Enrichment of the cord blood stem cells by optophoresis would allow for a smaller amount of material to be stored, which could be more easily given back to the patient or another host.

Adult stem cells from liver, neural tissue, bone marrow, and the Like. It is becoming increasingly clear that many mature tissues have small subpopulations of immortal stem cells which may be manipulated ex vivo and then can be reintroduced into a patient in order to repopulate a damaged tissue. Optophoresis can be used to purify these extremely rare adult stem cells so that they may be used for cell therapy applications.

Islet cells from pancreas. It has been proposed that for persons with diabetes resulting from lack of insulin production, the insulin producing beta islet cells from a healthy pancreas could be transplanted to restore that function to the diabetic person. These cells make up only a small fraction of the total donor pancreas. Optophoresis provides a method to enrich the islet cells and would be useful for preparation of this specific type of cell for transplantation.

Activated B or T cells. During an immune response either T or B white cell subsets which target a specific antigen become active. These specific activated cells may be required as separate components for use in ex vivo expansion to then be applied as immunotherapy products or to be gotten rid of, since activated B or T cells can cause unwanted immune reactions in a patient such as organ rejection, or autoimmune diseases such as lupus or rheumatoid arthritis. Optophoresis provides a method to obtain activated cells either to enrich and give back to a patient or to discard cells which are causing pathological destruction.

Dendritic cells. Dendritic cells are a subset of white blood cells which are critical to establishing a T-cell mediated immune response. Biotech and pharmaceutical companies are working on ways to harvest dendritic cells and use them ex vivo in conjunction with the appropriate antigen to produce a specific activated T cell response. Optophoresis would allow isolation of large numbers of dendritic cells for such work.

HPRT-cells. Hypoxanthine-guanine phosphoribosyltransferase (HPRT) is an enzyme which exits in many cells of the blood and is involved in the nucleoside scavenging pathway. Persons who have high mutation rates due to either endogenous genetic mutations or exogenous exposure to mutagens can be screened for HPRT lacking cells (HPRT-) which indicate a mutation has occurred in this gene. Optophoresis following screening by compounds which go through the HPRT system can be used to easily select HPRT minus cells and quantitate their numbers.

Viable or mobile sperm cells. Approximately 12% of couples are unable to initiate a pregnancy without some form of assistance or therapy. In about 30% these cases, the male appears to be singularly responsible. In an additional 20% of cases, both male and female factors can be identified. Thus, a male factor is partly responsible for difficulties in conception in roughly 50% of cases. The number of women aged 15–44 with impaired ability to have children is well over 6 million. Semen analysis is currently performed using a variety of tests and is based on a number of parameters including count, volume, pH, viscosity, motility and morphology. At present, semen analysis is a subjective and manual process. The results of semen analysis do not always clearly indicate if the male is contributing to the couple's infertility. Gradient centrifugation to isolate motile sperm is an inefficient process (10 to 20% recovery rate). Sperm selection is accomplished using either gradient centrifugation to isolate motile sperm used in In Utero Insemination (IUI) and In Vitro Fertilization (IVF) or visual inspection and selection to isolate morphologically correct sperm used in IVF and Intracytoplasmic Sperm Injection (ICSI). Each year in the U.S., 600,000 males seek medical assistance for infertility.

One of the reasons for male infertility is the lack of high enough percentages of viable and/or mobile sperm cells. Viable and/or mobile sperm cells can be selected using optophoresis and by enriching their numbers, higher rates of fertilization can be achieved. This application could also be used to select X from Y bearing sperm and vice versa, which would then be used selectively to induce pregnancies in animal applications where one sex of animal is vastly preferred for economic reasons (dairy cows need to be female, while it is preferable for meat producing cattle to be male for example).

Liposomes loaded with various compounds. A recent mode of therapeutic delivery of pharmaceutical products is to use liposomes as the delivery vehicle. It should be possible using optophoresis to separate liposomes with different levels of drug in them and to enrich for those liposomes in which the drugs are most concentrated.

Tissue Engineering, e.g., Cartilage precursors from fat cells. Tissue engineering involves the use of living cells to develop biological substitutes for tissue replacements which can be used in place of traditional synthetic implants. Loss of human tissue or organ function is a devastating problem for a patient and family. The goal of tissue engineering is to design and grow new tissue outside the body that could then be transplanted into the body.

A recent report has demonstrated that cells found in human adipose tissue can be used ex vivo to generate cartilage which can be used as a transplant material to repair damage in human joints. Optophoresis can be used to purify the cartilage forming cells from the other cells in adipose tissue for ex vivo expansion and eventual tissue engineering therapy.

Nanomanipulation of small numbers of cells. Recent miniaturization of many lab processes have resulted in many lab analyses being put onto smaller and smaller platforms, evolving towards a "lab-on-a-chip" approach. While manipulation of biomolecules in solution has become routine in such environments, manipulation of small numbers of cells in microchannel and other nano-devices has not been widely achieved. Optophoresis will allow cells to be moved in microchannels and directed into the region with the appropriate processes on the chip.

Cellular organelles; mitochondria, nucleus, ER, microsomes. The internal constituents of a cell consists of the cytoplasm and many organelles such as the mitochondria, nucleus, etc. Changes in the numbers or physical features of these organelles can be used to monitor changes in the physiology of the cell itself. Optophoresis can allow cells to be selected and enriched which have particular types, morphologies or numbers of a particular organelle.

Cow reticulocytes for BSE assays. It has been reported that a cellular component of the reticulocyte, EDRF, is found at elevated levels in the reticulocytes of cows infected with BSE (bovine spongiform encephalopathy). Reticulocytes are generally found at low levels in the blood and therefore the use of optophoresis would allow their enrichment and would increase the accuracy of diagnostic tests based on the quantitation of the EDRF mRNA or protein.

Monitoring

Growing/dividing cells vs. resting cells. Cells may be stimulated to grow by various growth factors or growth conditions. Most assays which exist for cell growth require the addition of external labeling reagents and/or significant time in culture before cell growth can be demonstrated. By using optophoresis, cells which have begun to divide will be identified, providing a rapid method for calculating how much of a given cell population is in the growth phase. Cells in different parts of the cell cycle should have different optical properties and these may be used to either sort cells based on where in the cycle they are as well as to determine what fraction of the total cell population is in each stage of the cell cycle.

Apoptotic cells. Cells which are undergoing programmed cell death or apoptosis can be used to identify specific drugs or other phenomenon which lead to this event. Optophoresis can be used to identify which cells are undergoing apoptosis and this knowledge can be used to screen novel molecules or cell conditions or interactions which promote apoptosis.

Cells with membrane channels open; change in membrane potentials. The outer membrane of many types of cells contain channels which facilitate the passage of ions and small molecules into and out of the cell. Movement of such molecules can lead to further changes in the cell such as changes in electrical potential, changes in levels of second messengers, etc. Knowledge of these changes can be useful in drug screening for compounds which modulate membrane channel activity. Optophoresis can be used to indicate when membrane channels are being perturbed by exogenous compounds.

Live vs. dead cells. Many applications exist which require the identification and quantitation of live versus dead cells. By using optophoresis dead cells can be identified and counted.

Virally infected cells. There are many diagnostic applications where it is important to measure cells which contain virus, including ones for CMV, HIV, etc. Optophoresis can be used to differentiate cells which contain virus from cells which do not.

Cells with abnormal nucleus or elevated DNA content. One of the hallmarks of a tumor cell is that it will contain either excess DNA, resulting in an abnormal size and/or shape to it's nucleus. By using optophoresis tuned to the nuclear content of a cell populations with abnormal amounts of DNA and/or nuclear structure may be identified and this information can be used as a diagnostic or prognostic indicator for cancer patients.

Cells decorated with antibodies. A large selection of commercially available antibodies exists which have specificities to cellular markers which define unique proteins and/or types of cells. Many diagnostic applications rely on the characterization of cell types by identifying what antibodies bind to their surface. Optophoresis can be used to detect when a cell has a specific antibody bound to it.

Cells with bound ligands, peptides, growth factors. Many compounds and proteins bind to receptors on the surface of specific cell types. Such ligands may then cause changes inside the cell. Many drug screens look for such interactions. Optophoresis provides a means to monitor binding of exogenous large and small molecules to the outside of the cell, as well as measurement of physiological changes inside the cell as a result of compound binding.

Bacteria for viability after antibiotic exposure. Microorganisms are often tested for sensitivity to a spectrum of antibiotics in order to determine the appropriate therapy to pursue to kill an infectious organism. Optophoresis can be used to monitor bacterial cells for viability and for cessation of growth following antibiotic exposure.

Drug screening on the NCI 60 panel. A panel of 60 tumor cell lines has been established by the National Cancer Institute as a screening tool to determine compounds which may have properties favorable to use as chemotherapeutic agents. It should be possible to use optophoresis to array all 60 lines and then to challenge them with known and novel chemicals and to monitor the cell lines for response to the chemicals.

Cells for cytoskeletal changes. The cytoskeleton is a complex of structural proteins which keeps the internal structure of the cell intact. Many drugs such as taxol, vincristine, etc. as well as other external stimuli such as temperature are known to cause the cytoskeleton to be disrupted and breakdown . Optophoresis provides a means to monitor populations of cells for perturbations in the cytoskeleton.

Beads with compounds bound to them, to measure interactions with the cell surface or with other beads. The interactions of microspheres with cells or other compounds has been used in a number of in vitro diagnostic applications. Compounds may be attached to beads and the interactions of the beads with cells or with beads with other compounds on them can be monitored by optophoresis.

Progenitor cell/colony forming assays. Progenitors are cells of a given tissue which can give rise to large numbers of more mature cells of that same tissue. A typical assay for measuring progenitor cells is to allow these cells to remain in culture and to count how many colonies of the appropriate mature cell type they form in a given time. This type of assay is slow and cumbersome sometimes taking weeks to perform. By using optophoresis to monitor the growth of a single cell, progenitor proliferation can be measured on a nano-scale and results should be obtained within a much shorter length of time.

Dose limiting toxicity screening. Almost all compounds are toxic at some level, and the specific levels of toxicity of compounds are identified by measuring at what concentration they kill living cells and organisms. By monitoring living cells with optophoresis as the dose of a compound is slowly increased, the level at which optical properties indicative of cell damage and/or death can be ascertained.

Monitor lipid composition/membrane fluidity in cells. The membranes of all cells are composed of lipids which must maintain both the proper degree of membrane fluidity at the same time that they maintain basic cell membrane integrity. Optophoresis should be able to measure the fluidity of the membrane and to provide information on compounds and conditions which can change membrane fluidity, causing membranes to be either more or less fluid.

Measure clotting/platelet aggregation. Components found in the blood such as platelets and clotting proteins are needed to facilitate blood clot formation under the appropriate circumstances. Clotting is often monitored in order to measure disease states or to assess basic blood physiology. Optophoresis can provide information on platelet aggregation and clot formation.

Certain of the data reported herein were generated with the following setup. Optical gradient fields were generated using a Michelson interferometer and either a 150 mW, 812 nm laser (812 system) or a 2.5 W, 1064 nm laser (1064 system). The 812 system used a 100× (1.25 NA) oil immersion lens to focus the fringe pattern and to visualize the sample. The 1064 system used a 20× objective to focus the fringes and a 60× objective to visualize the sample. In general the sample cell was a coated microscope slide and/or coverslip that was sealed with Vaseline. Coverslip spacers controlled the height of the cell at approximately 150 micrometers Coating Of Surfaces; Rain-X™, Agarose, CYTOP, Fluorosilane Scattering forces tend to push the particles or cells against the surface of the sample cell. Therefore, a number of surface coatings were evaluated to minimize nonspecific adhesion and frictional forces. Hydrophobic/hydrophilic and covalent/noncovalent surface treatments were evaluated.

Covalent/Hydrophobic Glass slides and coverslips were treated with perfluoro-octyltrichlorosilane (Aldrich, Milwaukee, Wis.) using solution or vapor deposition. Solution deposition was as follows: a 2–5% silane solution in ethanol, incubate 30 minutes at room temperature, rinse 3 times in ethanol and air dry. Vapor deposition involved applying equal volumes of silane and water in separate microcentrifuge tubes and sealing in a vacuum chamber with the substrate to be treated. Heat to 50° C., 15 hrs.

Noncovalent/Hydrophobic—A commercial water repellent containing polysiloxanes, Rain-X, was applied according to the manufacturer's instructions.

A liquid Teflon, CYTOP (CTL-107M, Wilmington, Del.) was spun coated using a microfuge. The CYTOP was diluted to 10% in fluorooctane (v/v) and 50 microliters was pipetted and spun for 5 seconds. This was repeated a second time and then air dried.

Noncovalent/Hydrophilic—Agarose hydrogel coatings were prepared as follows: melt 2% agarose in water, pipette 100 microliters to the substrate, spin for 5 seconds, bake at 37° C. for 30 minutes.

All of the coatings were effective when working with particles. The CYTOP was more effective at preventing adhesion when working with biological cells.

Separation By Size—Polystyrene particles (Bangs Labs, Fishers, Ind.) of different sizes (1, 3 and 5 micrometer diameter) were separated using moving optical gradient fields. Three and five micrometer diameter particles were diluted 1/500 in distilled water and ten microliters was pipetted onto a Rain-X coated slide. The 812 system was used to generate a spot size of 25–30 micrometers consisting of 4–5 fringe periods and moving at 15 micrometers/second.

Figure 32:
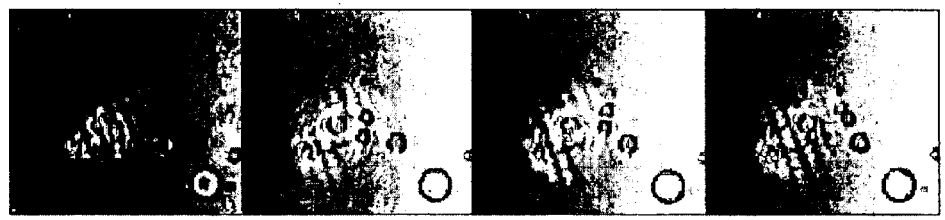
FIG. 32 shows time lapse photographs of an experiment separating particles by size with a moving optical gradient field.

FIG. 32 shows a sorting sequence at 1-second intervals with 3 and 5 micrometer polystyrene particles. The smaller, 3 micrometer diameter, particle was readily moved by the gradient fields whereas the larger, 5 micrometer diameter, particle was unaffected. The larger particle was not moved because it spanned multiple fringes so gradient forces were effectively cancelled. Similar results were obtained with 1 and 3 micrometer diameter particles.

Separation By Refractive Index—Polystyrene, polymethylmethacrylate and silica particles of similar size (~5 micrometer diameter, Bangs Labs) and refractive indexes of 1.59, 1.49 and 1.37, respectively, were sorted by moving optical gradient fields. Observed escape velocities for polystyrene, PMMA and silica were 44, 47 and 32 micrometers/second, respectively. Briefly, a particle is aligned in the fringe and the fringes are moved at increasing speed until the particle slips. This results in a semi-quantitative measurement of the total forces experienced by the particle, i.e. photonic, hydrodynamic and frictional. It will be appreciated by those skilled in the art that the absolute value of the escape velocity will differ depending upon system conditions, e.g., laser power. The numerical results provided herein are meant to provide measured data for the system actually used, and are not to be considered a limitation on the values which might exist in a different system.

Particles were diluted 1/500 in distilled water (n=1.33). The 812 system was used to generate a gradient field with a fringe period of 10 micrometers. Polystyrene and PMMA particles were sorted from silica particles by moving the gradient field at a threshold value of approximately 40 micrometers/second.

Separation By Surface Functionalization and Doping—Polystyrene particles (~6 micrometer diameter) colored with blue or pink dye were purchased from Polysciences, Inc. The pink particles also had carboxyl groups on the particle surface. The particles were diluted 1/500 in distilled water and 10 microliters was pipetted onto a Rain-X coated slide. The 812 system was used to generate a moving optical gradient field with a fringe period of approximately 12 micrometers. In the fringes, the pink particle moved preferentially.

Figure 33:
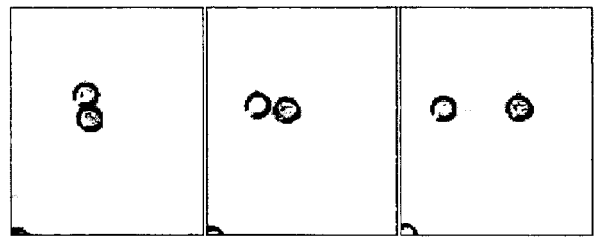
FIG. 33 shows time lapse photographs of an experiment separating particles by surface functionalization.

FIG. 33 shows the actual movement of the particles.

In another experiment, 1 micrometer latex beads labeled with biotin were used to determine changes in escape velocity when different ligands were attached. The biotin labeled beads were diluted 1/100 in PBS buffer. A 50 ul aliquot was incubated with an excess of streptavidin or 10 nanometer colloidal gold-streptavidin conjugate for 10 minutes. The beads were pelleted by centrifugation and resuspended in PBS buffer. Measured escape velocities, using the 1064 system, were 5.3, 4.3 and 3.6 micrometers/second for biotin labeled beads, beads with streptavidin and beads with streptavidin-colloidal gold, respectively.

Separation By Wavelength Resonance (812 vs. 1064 nm)—The above experiment with colored polystyrene particles was repeated using the 1064 system and the results were reversed. The blue particle was preferentially moved. Similar results were obtained when the 1064 system was set at 150 mW rather than 2.5 W. This suggests that wavelength tuning could enhance the discrimination process.

Separation By Index Matching—Silica and polystyrene particles (3 and 5 micrometer diameter, respectively) were diluted 1/500 in hydrophilic silicone (dimethylsiloxane-ethylene oxide block copolymer, Gelest, Inc., Tullytown, Pa.). The refractive index of the medium (n=1.44) was intermediate between the silica (n=1.37) and polystyrene (n=1.59) particles. The particle size was not important in this experiment.

Using the 1064 system, the gradient force was focused into a diffuse spot approx. 15 micrometers in diameter. More generally, for all of the systems and applications described herein, a defocused beam, such as a defocused laser beam may be utilized. Preferably, the beam is defocused such that the spot or beam size is on the order of magnitude of the size of the particle. For cells, the size would be approximately 10 to 20 microns. The polystyene particle moved towards the gradient field while the silica particle moved away from it. This demonstrated that the suspending medium could be changed to optimize separation.

Separation Red Blood Cells vs. Retic

A reticulocyte control (Retic-Chex) was obtained from Streck Labs. A sample containing 6% reticulocytes was stained for 15 minute s with New Methylene Blue for 15 minutes, a nucleic acid stain that differentially stains the reticulocytes versus the unnucleated red blood cells. The sample was diluted 1/200 in PBS and mounted on a fluorosilane coated slide The 812 system was used to generate optical gradient fields. The fringe period was adjusted to 15 micrometers and was moved at 15 micrometers/second. The reticulocytes were preferentially moved relative to red blood cells.

Separation of White Blood Cells vs. Red Blood Cells

A whole blood control (Para12 Plus) was obtained from Streck Labs. The sample was stained for 15 minutes with New Methylene Blue, a nucleic acid stain that differentially stains the nucleated white blood cells versus the unnucleated red blood cells. The sample was diluted 1/200 in PBS and mounted on a fluorosilane coated slide. The 812 system was used to generate optical gradient fields. The fringe period was adjusted to 15 micrometers and was moved at 22 micrometers/second. The white blood cells were moved by the fringes while the red blood cells were not.

Separation of Leukemia vs. Red Blood Cells

One milliliter of the leukemia cell line U937 suspension was pelleted and resuspended in 100 microliters PBS containing 1% BSA. Equal volumes of U937 and a 1/200 dilution of red blood cells were mixed together and 10 microliters was placed on a CYTOP coated slide. Separate measurements with moving fringe fields showed that the escape velocity for U937 cells was sigificantly higher than the escape velocity for red blood cells, 60 and 23 micrometers/second, respectively. The 1064 system was used to generate optical gradient fields with a fringe period of approximately 30 micrometers and moving at 45 micrometers/second, an intermediate fringe velocity. As expected the U937 cells move with the fringes and the red blood cells do not. In one embodiment, the moving fringe may be reduced to a single peak. Preferably, the peak is in the form of a line. In operation, a slow sweep (i.e., at less than the escape velocity of the population of particles) is made across the region to be interrogated. This causes the particles to line up. Next, the fringe is moved quickly (ie, at a speed greater than the escape velocity of at least some of the particle in the population), preferably in the direction opposite the slow sweep. This causes the selective separation of those particles having a higher escape velocity from those having a lower escape velocity. Optionally, the remaining line of particles may then be again interrogated at an intermediate fringe velocity. While this technique has general applicability to all of the applications and systems described herein, it has been successfully implemented for the separation of U937 cells from red blood cells.

Sorting of Red Blood Cells vs. Polystyrene Particles in Microchannels

Glass microchannels with an "H" configuration (see FIG. 16) were used to demonstrate sorting of red blood cells and 6 micrometer polystyrene particles. The channels were purchased from Agilent (DNA 500 LabChip) and were 40 micrometers wide and 10 micrometers deep. Unwanted or unused channels and reservoir ports were blocked by backfilling with Norland 61 optical adhesive followed by UV and thermal curing. The channels were primed with ethanol, followed by water and finally by PBS buffer with 1% BSA. The inlet reservoirs were built up about 1 mm higher than the outlet reservoirs. Flow rates were controlled by a combination of pressure and electrokinetic forces. A Keithley 236 power supply was used to apply an electric field between 5 and 10 V/cm.

A 1/200 mixture of red blood cells and particles in PBS buffer, 1% BSA was added to an inlet reservoir and an equal volume of PBS buffer, 1% BSA was added to the other inlet reservoir. The gradient field was positioned in the crossbar of the "H" near the downstream junction. The 1064 system was fitted with a cylindrical lens to increase the aspect ratio of the gradient field. The resultant gradient field was approximately 40 micrometers wide by 80 micrometers long with a fringe period of 12 ums and moving at 30 micrometers/second.

In the absence of or with a nonmoving optical gradient field, the cells and particles remain in the top half of the "H" channel and exit via the upper outlet. In the presence of a moving optical gradient field, the particles are diverted to the lower outlet arm and are sorted from the red blood cells.

The flow rate was adjusted to approximately 80 micrometers/second. The sorting process was digitally recorded and subsequently analyzed. Out of 132 possible sorting events (121 red blood cells and 11 particles), 2 red blood cells and no particles were mis-sorted. The sort rate was approximately 2/second.

Sorting of Red Blood Cells vs. White Blood Cells in Microchannels

Figure 36:
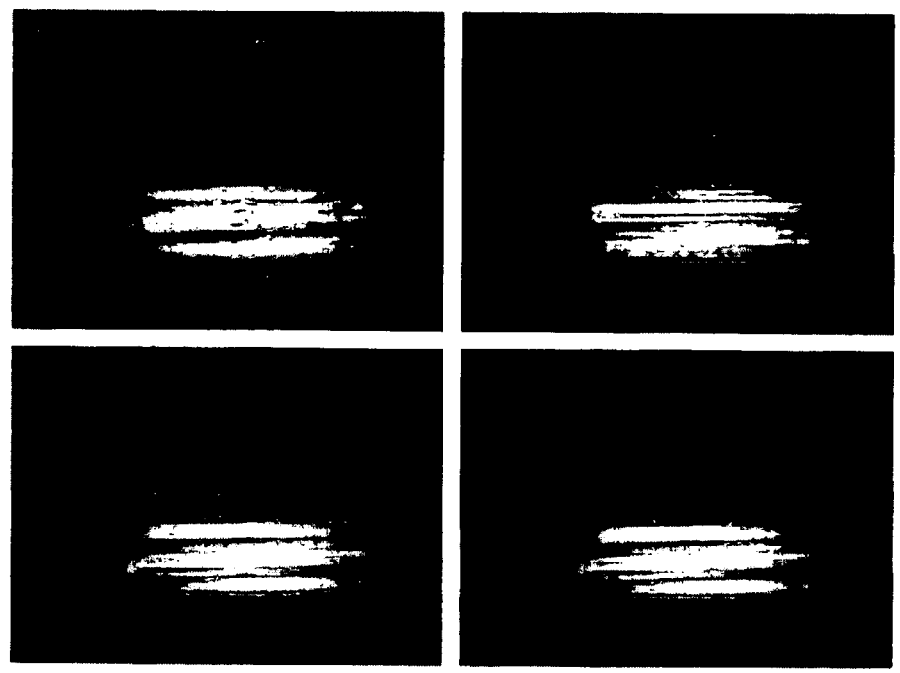
FIG. 36 shows photographs of sorting of two cell types in a microchannel device. 1 shows a red blood cell and a white blood cell successively entering the moving optical gradient field. 2 shows that white blood cell has been translated down by the action of the moving optical gradient field while the red blood cell has escaped translation. 3 and 4 show that the red blood cell and white blood cell continue to flow into separate channels, completing the sorting.

FIG. 36 shows photographs of sorting of two cell types in a microchannel device. 1 shows a red blood cell and a white blood cell successively entering the moving optical gradient field. 2 shows that white blood cell has been translated down by the action of the moving optical gradient field while the red blood cell has escaped translation. 3 and 4 show that the red blood cell and white blood cell continue to flow into separate channels, completing the sorting.

Gradient Force Manipulation of Liposomes

Fluorescently labeled liposomes, approximately 0.2 micrometers in diameter, were obtained from a B-D Qtest Strep kit. Ten microliters was placed in a Rain-X coated slide and the 1064 system was used to generate an optical gradient field. A 15 mW 532 nm diode laser was also focused through the objective to visualize the liposome fluorescence. When a standing gradient field was projected onto the sample, fluorescence was more intense in this area. This suggests that the liposomes were moving towards the gradient field.

Differential Motion Imaging

Figure 34:
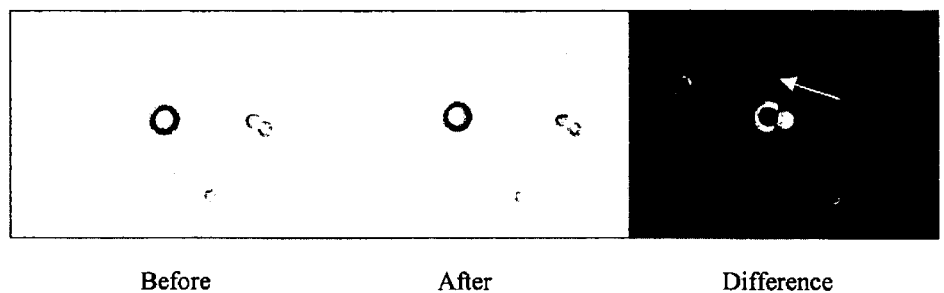
FIG. 34 shows a Before, After and Difference photograph of particles subject to a moving optical gradient field.

Polystyrene and silica particles were diluted in distilled water. As shown in the photographs of FIG. 34, a "before" image was captured using a CCD camera and Image Pro Express software. A moving optical gradient field generated by the 1064 system was scanned over the particles. Another image (an "After" image) was captured and the "before" image was subtracted. The resultant image (labeled "Difference") clearly identifies that the polystyrene particle had moved.

Escape Velocities of Different Cell Types

Escape velocities were measured using a gradient field generated by the 1064 system on CYTOP coated coverslips.

| Cell Type | Escape Velocity (um/sec.) |
| --- | --- |
| Red Blood Cell | 5.6 +/− 0.4 |
| White Blood Cell | 11.0 +/− 1.8 |
| Chicken Blood (Retic. Model) | 7.3 +/− 1.4 |

-continued

| Cell Type | Escape Velocity (um/sec.) |
| --- | --- |
| K562 Cells, No Taxol Treatment | 10.0 +/− 0.7 |
| K562 Cells, 26 Hr. Taxol Treatment | 8.2 +/− 0.4 |

K562 Cells: Chronic myelogenous leukemia, lymphoblast

Figure 35:
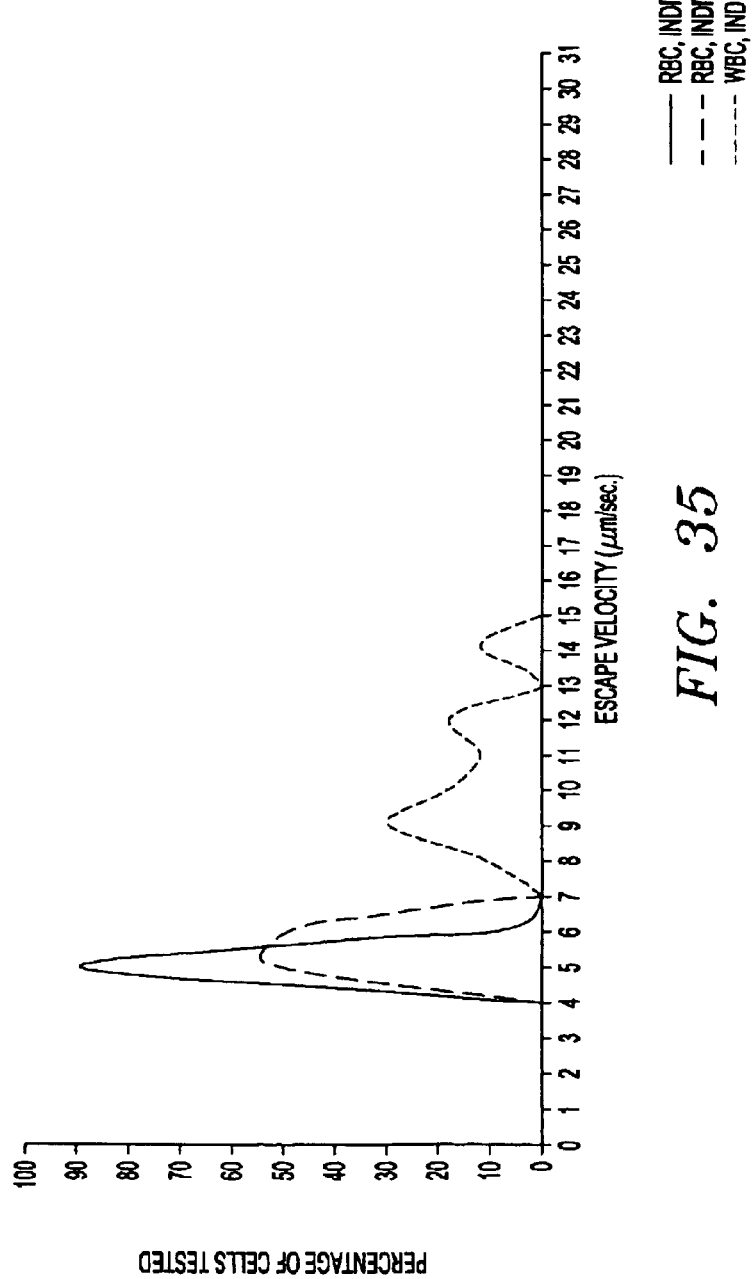
FIG. 35 is a graph of percent of cells measured in an experiment versus escape velocity, for a variety of cell types.

FIG. 35 shows a graph of percent of cells measured as a function of escape velocity ($\mu$m/second).

Separation of Treated and Untreated Leukemia Cells

PMA was dissolved in ethanol at a concentration of 5 mg/mL. 3 mls of U937 cells grown in RPMI 1640 media with supplements were removed from the culture flask and 1 ml was placed into each of three eppendorf tubes. Cells from the first tube were pelleted for 4 minutes at 10,000 rpm and resuspended in 250 uL PBS/1%BSA buffer for escape velocity measurements. PMA was added to the remaining two tubes of U937 cells to a final concentration of 5 ug/mL. These tubes were vortexed and placed in a 37° C. water bath for either one hour or six hours. At the end of the time point, the tube was removed, cells were pelleted and then resuspended as described above and escape velocity measurements taken. The cells treated for 6 hours had a significantly higher escape velocity as compared to the untreated cells.

While preferred embodiments and methods have been shown and described, it will be apparent to one of ordinary skill in the art that numerous alterations may be made without departing from the spirit or scope of the invention. Therefore, the invention is not limited except in accordance with the following claims.

We claim:

1. A method for sorting a particle of interest from a plurality of particles comprising the steps of:

determining an absorption maxima of the particle of interest;

providing a light source to generate a beam of coherent light at a wavelength of the absorption maxima;

providing a plurality of particles on a support surface;

illuminating the plurality of particles with a moving beam of the coherent light, the moving beam of light causing differential movement between the particle of interest and the plurality of partici s; and collecting the particle of interest.

2. The method of claim 1, wherein the absorption maxima is a local maxima.

3. The method of claim 1, wherein the absorption maxima is a global maxima.

4. The method of claim 1, wherein the absorption maxima is obtained by empirical data.

5. The method of claim 1, wherein the support surface is a slide.

6. The method of claim 1, wherein the support surface is a microfluidic channel.

* * * * *